(12) United States Patent
Sabeg et al.

(10) Patent No.: US 12,102,058 B2
(45) Date of Patent: Oct. 1, 2024

(54) AUTOMATED INSECT REARING FACILITY, CONTAINER, AND MODULES

(71) Applicant: Beetle Genius, SPRL, Etterbeek (BE)

(72) Inventors: Karim Sabeg, Brussels (BE); Manuel Capote, Seville (ES); Ricardo Trevino, Seville (ES); Antonio Coronel, Seville (ES)

(73) Assignee: Beetle Genius, SPRL, Etterbeek (BE)

( * ) Notice: Subject to any disclaimer, the term of this patent is extended or adjusted under 35 U.S.C. 154(b) by 898 days.

(21) Appl. No.: 16/844,416

(22) Filed: Apr. 9, 2020

(65) Prior Publication Data

US 2020/0323173 A1 Oct. 15, 2020

Related U.S. Application Data

(60) Provisional application No. 62/913,334, filed on Oct. 10, 2019, provisional application No. 62/831,815, filed on Apr. 10, 2019, provisional application No. 62/831,906, filed on Apr. 10, 2019, provisional application No. 62/831,932, filed on Apr. 10, 2019.

(51) Int. Cl.
*A01K 29/00* (2006.01)
*A01K 1/00* (2006.01)
*A01K 67/033* (2006.01)

(52) U.S. Cl.
CPC .......... *A01K 29/005* (2013.01); *A01K 1/0076* (2013.01); *A01K 67/033* (2013.01); *A01K 1/0082* (2013.01); *A01K 2227/706* (2013.01)

(58) Field of Classification Search
CPC .. A01K 67/033; A01K 1/0082; A01K 1/0076; A01K 2227/706; A01K 29/005
See application file for complete search history.

(56) References Cited

U.S. PATENT DOCUMENTS

| | | | |
|---|---|---|---|
| 6,244,213 B1 | 6/2001 | Tedders et al. | |
| 7,861,672 B2 | 1/2011 | Power | |
| 8,403,614 B2 | 3/2013 | Bastian, II et al. | |
| 9,629,339 B2* | 4/2017 | Newton | A01K 5/00 |
| 9,642,344 B2 | 5/2017 | Unger | |
| 10,159,229 B2 | 12/2018 | Merchant et al. | |
| 10,188,086 B2 | 1/2019 | Leo | |
| 10,362,772 B2* | 7/2019 | Arsiwalla | A01K 67/033 |

(Continued)

FOREIGN PATENT DOCUMENTS

| | | |
|---|---|---|
| CN | 102578030 | 7/2012 |
| CN | 105028974 | 11/2015 |

(Continued)

*Primary Examiner* — Monica L Perry
*Assistant Examiner* — Aaron M Rodziwicz
(74) *Attorney, Agent, or Firm* — K&L Gates LLP

(57) ABSTRACT

An automated insect rearing facility for the reproduction and growth of insects, and in particular, *Tenebrio molitor* larvae is disclosed herein. The insect rearing facility includes insect rearing containers that automate insect rearing activities and regulate environmental conditions for insect growth. The facility and container include components that are in communication with a control unit, which directs and controls the components according to predetermined instructions and/or in response to feedback from a number of various sensors. The components may autonomously perform a multitude of facility operations without the need for human intervention.

17 Claims, 20 Drawing Sheets

(56) References Cited

U.S. PATENT DOCUMENTS

| | | | |
|---|---|---|---|
| 10,405,528 B2* | 9/2019 | Comparat | B65G 1/0407 |
| 10,842,138 B1* | 11/2020 | Lolley | A01K 67/033 |
| 2011/0081452 A1 | 4/2011 | Hem et al. | |
| 2016/0066552 A1 | 3/2016 | Arsiwalla et al. | |
| 2017/0354178 A1 | 12/2017 | Armenjon et al. | |
| 2018/0002452 A1 | 1/2018 | Berezina et al. | |
| 2018/0016357 A1 | 1/2018 | Berezina et al. | |
| 2018/0070566 A1 | 3/2018 | Comparat et al. | |
| 2018/0077912 A1 | 3/2018 | Comparat et al. | |
| 2018/0271072 A1 | 9/2018 | Sobecki et al. | |
| 2018/0303126 A1 | 10/2018 | Hubert et al. | |
| 2019/0358271 A1 | 11/2019 | Motte et al. | |
| 2020/0253176 A1* | 8/2020 | Fotiadis | A23K 10/26 |
| 2021/0212300 A1* | 7/2021 | Maurits | A01K 67/033 |

FOREIGN PATENT DOCUMENTS

| | | | |
|---|---|---|---|
| WO | WO-2012115959 A2 * | 8/2012 | A01K 29/00 |
| WO | WO2018134524 | 7/2018 | |

\* cited by examiner

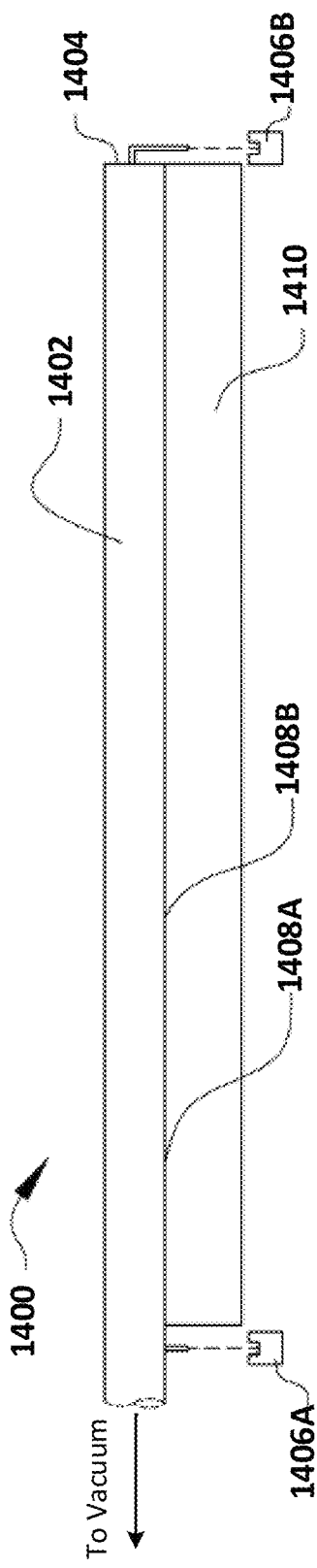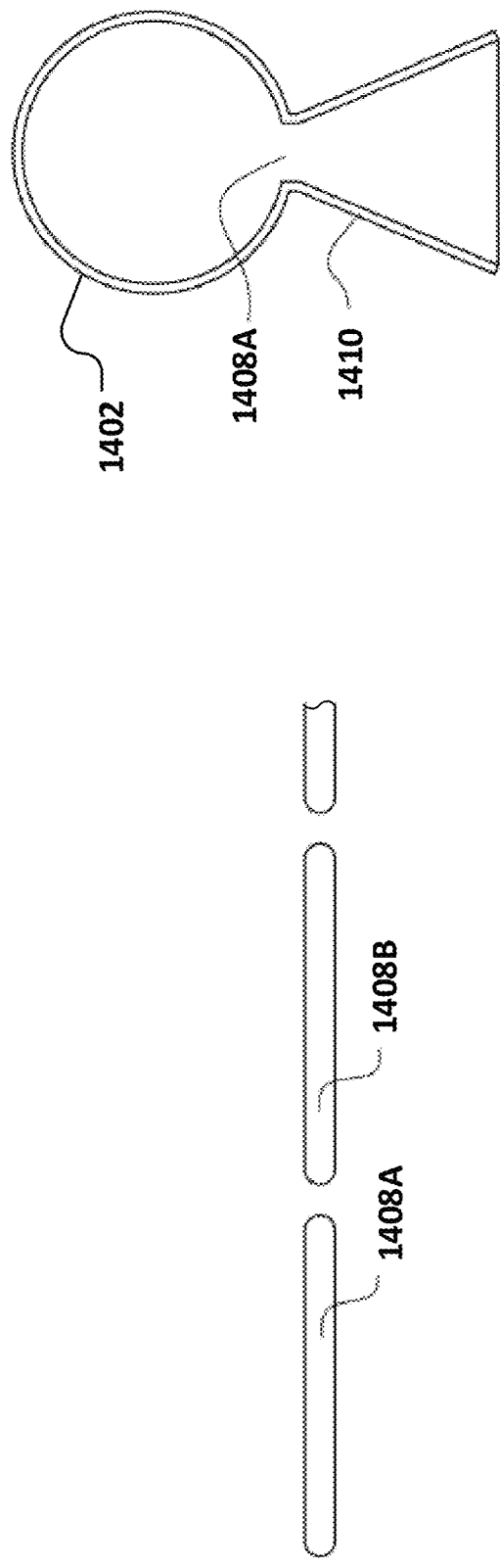

AUTOMATED INSECT REARING FACILITY, CONTAINER, AND MODULES

PRIORITY CLAIM

The present application claims priority to and the benefit of U.S. Provisional Application No. 62/831,815, filed Apr. 10, 2019, U.S. Provisional Application No. 62/831,906, filed Apr. 10, 2019, U.S. Provisional Application No. 62/831,932, filed Apr. 10, 2019, and U.S. Provisional Application No. 62/913,334, filed Oct. 10, 2019, the entirety of each is herein incorporated by reference.

BACKGROUND

Insect farming includes the breeding of insects for substances that the insects produce, or for the insects themselves for use as a food source, dye, animal feed, or otherwise. Adult insects are bred to produce larvae eggs, which hatch into larvae. Food and water are provided to the larvae to facilitate growth and development. After some amount of time (e.g., six weeks), a larva initiates the process of metamorphosis into pupae and then into an adult insect. Before the larvae transform into pupae, in their final developmental stage, a large portion of the larvae are collected to be processed into a rich protein source and fatty oils, which can be provided as a human-grade food source or as animal feed. A small portion of the larvae are allowed to mature into adult insects so that they may breed and produce additional larvae eggs. This ensures the self-sustainability of the farm's insect colony. Additionally, larvae shed their skins on multiple occasions during the larvae growing process, which may be recovered to be used in a chitin generation process. Larvae excrements may also be collected to be used as a raw material to produce organic fertilizer (e.g., frass).

The *Tenebrio molitor*, commonly referred to as the flour worm, is best known for its larval form and is a species of Coleoptera of the Tenebrionidae family. The flour worm itself is commonly used as living food for exotic insectivorous pets such as reptiles and birds. It is also often used as fishing bait and is normally sold in pet stores in a container full of bran. Flour worms have a large lipid component because they need energy reserves during their metamorphosis so that an abuse in diet can cause imbalances in their metabolism.

The *Tenebrio molitor* is a natural source of proteins and fats that can metabolise a wide spectrum of sources of plant origin. The high concentration of proteins in its composition and a lipid profile that includes most of the essential fatty acids for animals (and humans), make it a food with interesting nutritional characteristics, so that the development of *Tenebrio molitor* as a food is increasingly valued by society.

There are a number of considerations for maximizing the output and efficiency of insect farming. For instance, three farming environment conditions must be taken in to account: temperature, light, and ventilation. The farming environment should be maintained at a particular temperature conducive to insect breeding and growth, have low light without any direct sunlight, and should be adequately ventilated, which may include forced ventilation. The farming environment's humidity can also be taken into account. In addition to the environmental conditions, food and water must be occasionally provided to the larvae and to some adult insects (some adult insect species do not eat). Insect excrement must also be occasionally removed from the larvae and/or adult insect environment. Maintaining these environmental conditions within desired ranges, and sufficiently providing food and water, may consume a significant amount of resources for the purpose of inducing maximum adult insect breeding and larvae growth.

An additional consideration for maximizing insect farming output and efficiency is collecting larvae for processing when the larvae are in their final developmental stage and prior to initiating pupae metamorphosis. Collecting the larvae as far along the final developmental stage as possible maximizes the amount of protein and fatty oils that can be produced from the larvae. The amount of time it takes larvae to develop before initiating pupae metamorphosis can be approximated. However, it may not be entirely consistent among larvae depending on the above-described environmental conditions and provided food and water.

In known insect farming operations, larvae and adult insects may be housed within containers that are components in a larger facility. The insect farming facility may include all of the components required in the insect farming operation, such as a food source, water source, temperature control, etc. A typical insect farming facility may therefore be large and manage a great quantity of insects. These known insect farming facilities, however, require some to most of the operations described above to be manually performed by facility workers. In part, given the large number of daily tasks required in a typical insect farming facility, the tasks are not always performed in the most effective or efficient manner, which may limit the facility's output and efficiency.

Additionally, known insect farming facilities are fixed facilities that cannot be transported from one place to another. For example, an insect farming facility may be a warehouse-type building with various operation components dispersed around the building. To transport the farming facility would require transferring the entire building or transferring each of the individual components to a different building equally equipped for the insect farming operations. Such transportation is not feasible in most or all typical situations.

Another drawback to some typical insect farming facilities is that insects are fed by blowing feed onto the insects. This may generate a large amount of dust, and may create a potentially explosive atmosphere. Such a feeding method also does not ensure the presence of a substrate bed that insects need.

Additionally, the *Tenebrio molitor* in particular is typically fed mainly by wheat bran complemented with other cereal derivatives such as soy meal and corn. The cost of raw materials can be expensive. Another typical problem is that changes are occurring in marine ecosystems, mainly due to wastewater, with the proliferation of algae with high rates of growth known as invasive algae. Invasive algae can colonize the seafloor displacing native species with significant losses to biodiversity. In addition to the impact on fishing, especially with nets, the swimmers' beaches are affected by the arrival of algae at the coasts.

Accordingly, it is an object of the present invention to overcome the above-described drawbacks of typical insect farming facilities, and in particular of *Tenebrio molitor* farming.

SUMMARY

The present disclosure provides a new and innovative automated insect rearing facility, container, and module for the reproduction and growth of insects. In an example, a system includes a container, a vacuum aspiration system, and a control unit for the rearing of *Tenebrio molitor* larvae.

In light of the disclosure herein and without limiting the disclosure in any way, in a first aspect of the present disclosure, which may be combined with any other aspect listed herein unless specified otherwise, a system for automatically controlling insect rearing activities includes a container including one or more modules configured with a plurality of trays. The plurality of trays are partitioned into sets of trays having an upper tray with a sieved base and a lower tray to receive first objects that fall through the sieved base of the upper tray. The system also includes a vacuum aspiration system including a vacuum and a plurality of sets of aspiration arms including a first aspiration arm and a second aspiration arm. The plurality of sets of aspiration arms are configured to aspirate second objects through the first aspiration arm from the respective upper tray to a first collection tank and the first objects through the second aspiration arm from the respective lower tray to a second collection tank. The system further includes a control unit programmed to control the plurality of sets of aspiration arms to collect the objects from the respective trays of the plurality of trays.

In accordance with a second aspect of the present disclosure, which may be used in combination with any other aspect listed herein unless stated otherwise, the container further includes one or more openings, wherein access to the one or more modules through the one or more openings is controlled by at least one retractable hatch, a light source configured to provide light to the interior of the container, at least one ventilation grille to allow air to enter the container, at least one air conditioning unit configured to maintain or adjust an internal humidity and internal temperature of the container, a light sensor configured to sense a lighting level in the container, a humidity sensor configured to sense the internal humidity of the container, and a temperature sensor configured to sense the internal temperature of the container.

In accordance with a third aspect of the present disclosure, which may be used in combination with any other aspect listed herein unless stated otherwise, the control unit is programmed to at least one of activate the at least one retractable hatch to open or close, adjust a lighting level output of the light source in response to feedback from the light sensor, adjust a humidity level output of the at least one air conditioning unit in response to feedback from the humidity sensor, or adjust a temperature level output of the at least one air conditioning unit in response to feedback from the temperature sensor.

In accordance with a fourth aspect of the present disclosure, which may be used in combination with any other aspect listed herein unless stated otherwise, the control unit is programmed to adjust the temperature level output to a temperature between 25 and 30 degrees Celsius.

In accordance with a fifth aspect of the present disclosure, which may be used in combination with any other aspect listed herein unless stated otherwise, the control unit is programmed to adjust the humidity level output to a humidity between 60% and 70%.

In accordance with a sixth aspect of the present disclosure, which may be used in combination with any other aspect listed herein unless stated otherwise, the container further includes a feed distribution network configured to distribute feed from a feed source to the plurality of upper trays, a water distribution network configured to distribute water from a water source to the plurality of upper trays, a plurality of weight sensors configured to sense a respective weight of contents in a respective upper or lower tray of the plurality of upper trays, and a plurality of moisture sensors configured to sense a respective moisture level in a respective upper or lower tray of the plurality of upper trays.

In accordance with a seventh aspect of the present disclosure, which may be used in combination with any other aspect listed herein unless stated otherwise, the control unit is programmed to at least one of activate the feed distribution network to distribute feed to a respective upper tray of the plurality of trays in response to feedback from the plurality of weight sensors; or activate the water distribution network to distribute water to a respective upper tray of the plurality of trays in response to feedback from the plurality of moisture sensors.

In accordance with an eighth aspect of the present disclosure, which may be used in combination with any other aspect listed herein unless stated otherwise, the feed distribution network is configured to simultaneously distribute feed to each of the respective upper trays of the plurality of trays.

In accordance with a ninth aspect of the present disclosure, which may be used in combination with any other aspect listed herein unless stated otherwise, the water distribution network is configured to simultaneously distribute water to each of the respective upper trays of the plurality of trays.

In accordance with a tenth aspect of the present disclosure, which may be used in combination with any other aspect listed herein unless stated otherwise, the control unit is programmed to activate the feed distribution network to distribute feed to a respective upper tray by opening a valve of the feed distribution network corresponding to the respective upper tray.

In accordance with an eleventh aspect of the present disclosure, which may be used in combination with any other aspect listed herein unless stated otherwise, the control unit is programmed to control the plurality of sets of aspiration arms to collect the objects from respective trays of the plurality of trays in response to at least one of a predetermined time elapsing or feedback from the plurality of weight sensors.

In accordance with a twelfth aspect of the present disclosure, which may be used in combination with any other aspect listed herein unless stated otherwise, the container is capable of being transported from a first location to a second location.

In accordance with a thirteenth aspect of the present disclosure, which may be used in combination with any other aspect listed herein unless stated otherwise, the upper trays are connected to an actuator for shacking or agitating the upper trays, and the control unit is programmed to cause the actuator to shake or agitate the upper trays.

In accordance with a fourteenth aspect of the present disclosure, which may be used in combination with any other aspect listed herein unless stated otherwise, the one or more modules includes at least one reproduction module and at least one growth module, the reproduction module having upper trays with the sieved bases that include perforations with a first diameter, the growth module having upper trays with the sieved bases that include perforations with a second diameter, wherein the first diameter is greater than the second diameter.

In accordance with a fifteenth aspect of the present disclosure, which may be used in combination with any other aspect listed herein unless stated otherwise, the container further includes a video sensor configured to detect one or more first objects including insect eggs in the lower trays, wherein the control unit is programmed to control the plurality of sets of aspiration arms to collect insect eggs from one or more respective lower trays of the plurality of trays in response to feedback from at least one of a plurality of weight sensors or the video sensor.

In accordance with a sixteenth aspect of the present disclosure, which may be used in combination with any other aspect listed herein unless stated otherwise, the container further includes a plurality of motion sensors configured to detect movement, wherein the control unit is programmed to control the plurality of sets of aspiration arms to collect insect larva second objects from one or more respective upper trays of the plurality of trays in response to feedback from the plurality of motion sensors.

In accordance with a seventeenth aspect of the present disclosure, which may be used in combination with any other aspect listed herein unless stated otherwise, the first objects aspirated through the respective second aspiration arms are at least one of insect eggs, insect larva, and waste, and the second objects aspirated through the respective first aspiration arms are at least one of insects and insect larva.

In accordance with an eighteenth aspect of the present disclosure, which may be used in combination with any other aspect listed herein unless stated otherwise, the container further includes an air extractor configured to direct air within the container outside of the container.

In accordance with a nineteenth aspect of the present disclosure, which may be used in combination with any other aspect listed herein unless stated otherwise, a container for automatically controlling insect rearing activities includes one or more modules configured with a plurality of trays, a light source configured to provide light to the interior of the container, an air extractor configured to direct air within the container outside of the container, at least one ventilation grille to allow air to enter the container, at least one air conditioning unit configured to maintain or adjust an internal humidity and internal temperature of the container, a feed distribution network configured to distribute feed from a feed source to the plurality of trays, a water distribution network configured to distribute water from a water source to the plurality of trays, a light sensor configured to sense a lighting level in the container, a humidity sensor configured to sense the internal humidity of the container, a temperature sensor configured to sense the internal temperature of the container, a plurality of weight sensors configured to sense a respective weight of contents in a respective tray of the plurality of trays, a plurality of moisture sensors configured to sense a respective moisture level in a respective tray of the plurality of trays, and a control unit for controlling an internal environment of the container and insect rearing activities. The control unit is programmed to adjust a lighting level output of the light source in response to feedback from the light sensor, adjust a humidity level output of the at least one air conditioning unit in response to feedback from the humidity sensor, adjust a temperature level output out the at least one air conditioning unit in response to feedback from the temperature sensor, activate the feed distribution network to distribute feed to a respective tray of the plurality of trays in response to feedback from the plurality of weight sensors, and activate the water distribution network to distribute water to a respective tray of the plurality of trays in response to feedback from the plurality of moisture sensors.

In accordance with a twentieth aspect of the present disclosure, which may be used in combination with any other aspect listed herein unless stated otherwise, the container further includes one or more openings, wherein access to one or more modules through the one or more openings is controlled by at least one retractable hatch, and wherein the control unit is programmed to activate the at least one retractable hatch to open or close.

In accordance with a twenty-first aspect of the present disclosure, which may be used in combination with any other aspect listed herein unless stated otherwise, the plurality of trays are partitioned into sets of trays having an upper tray with a sieved base and a lower tray to receive items that fall through the sieved base of the upper tray. The system further includes a vacuum aspiration system including a vacuum and a plurality of sets of aspiration arms including a first aspiration arm and a second aspiration arm. The plurality of sets of aspiration arms are configured to aspirate objects through the first aspiration arm from the respective upper tray to a first collection tank and through the second aspiration arm from the respective lower tray to a second collection tank, wherein the control unit is programmed to control the plurality of sets of aspiration arms to collect objects from respective trays of the plurality of trays.

In accordance with a twenty-second aspect of the present disclosure, which may be used in combination with any other aspect listed herein unless stated otherwise, the feed includes dried algae and has a composition that includes 18-24% of protein, 2-4% of fat, 50-70% of carbohydrates, 5-20% of moisture, and 1-8% of ash.

In accordance with a twenty-third aspect of the present disclosure, which may be used in combination with any other aspect listed herein unless stated otherwise, any of the structure, functionality, and alternatives disclosed in connection with any one or more of FIGS. 1 to 20 may be combined with any other structure, functionality, and alternatives disclosed in connection with any other one or more of FIGS. 1 to 20.

In light of the present disclosure and the above aspects, it is therefore an advantage of the present disclosure to provide an improved automated insect rearing facility, container, and module for the reproduction and growth of insects, and in particular *Tenebrio molitor* larvae.

It is another advantage of the present disclosure to provide an algae-based feed composition that improves a growth of *Tenebrio molitor* larvae.

The advantages discussed herein may be found in one, or some, and perhaps not all of the embodiments disclosed herein. Additional features and advantages are described herein, and will be apparent from the following Detailed Description and the figures.

BRIEF DESCRIPTION OF THE DRAWINGS

FIGS. 14A to 14C illustrate schematics of the components of an aspiration arm, according to an aspect of the present disclosure.

DETAILED DESCRIPTION

The present disclosure provides an automated insect rearing facility for the reproduction and growth of insects. In at least one example, the insects farmed at the provided facility are of the coleoptera order of insects (e.g., beetles), such as the *Tenebrio molitor* beetle, more commonly known as the mealworm beetle. In other examples, the provided facility may be utilized to farm other suitable insects, such as flies. The insects are farmed within rearing modules that contain sets of trays. The provided facility includes components that are in communication with a control unit, which directs and controls the components according to predetermined instructions and/or in response to feedback from a number of various sensors. The sensors may include light sensors, humidity sensors, temperature sensors, weight sensors, moisture sensors, motion sensors, and/or video sensors among other suitable sensors. The components may therefore autonomously perform the multitude of facility operations via direction from the control unit, without the need for human intervention. The facility also includes a feed source, a water source, temperature control, humidity control, and other processing equipment for producing products from the insects, insect skins, larvae, insect excrement, etc.

In some aspects, the modules may be housed within, or may be a component of, a container, which is disclosed herein. The example container may include many or all of the above-described facility components to autonomously provide insect rearing activities. The provided container may additionally configured such that it is capable of being transported from one location to another, thus providing mobility to the insect rearing operation. For instance, in one example, the provided container is configured as an intermodal ISO-standard shipping container. In some instances, the container may be transported to a customer site for producing insect-related products, such as animal feed for a specified duration of time.

Throughout this disclosure, "insects" may refer interchangeably to either larvae eggs, larvae, pupae, and/or adult insects. Further, disclosure is made in reference to the *Tenebrio molitor* beetle. However, the disclosed insect rearing system may be provided for other insect types, with adjustments made based on lighting/humidity/temperature levels, feed type, amount of water provided, and time allocated for growth.

Figure 1:
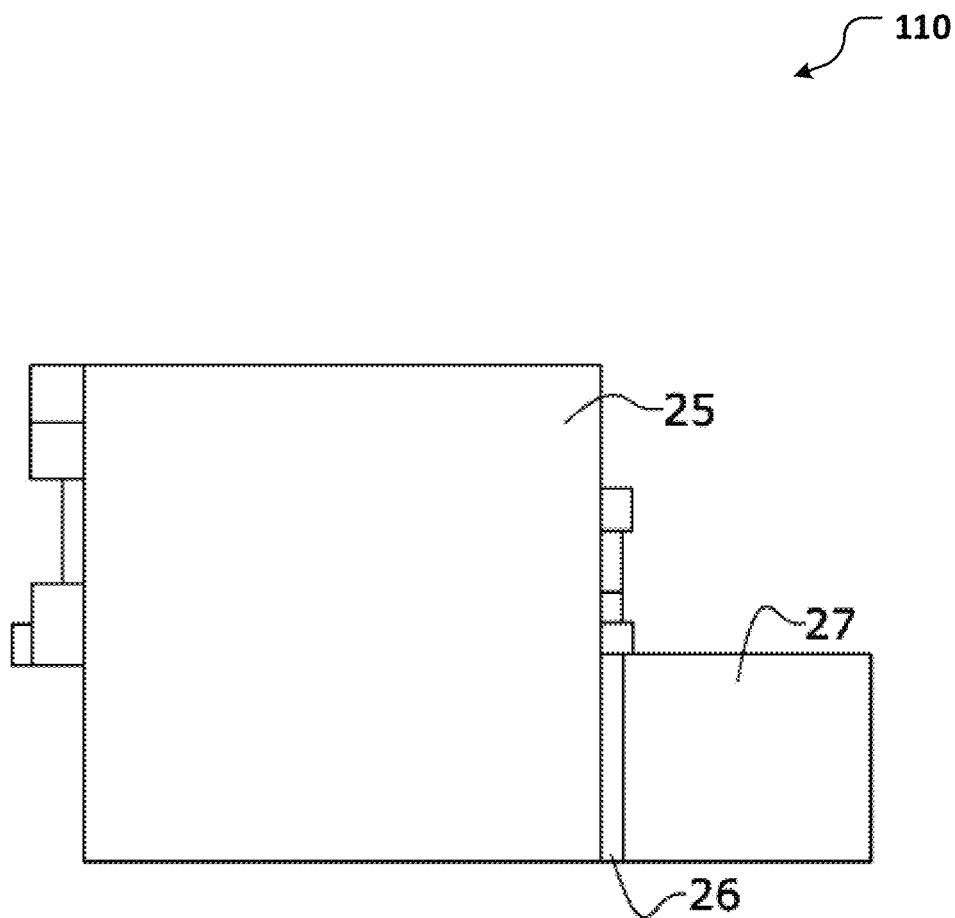
FIG. 1 illustrates a schematic of an example insect rearing facility, according to an aspect of the present disclosure.

FIG. 1 illustrates a schematic of an example insect rearing facility 110, according to an example embodiment of the present disclosure. The example insect rearing facility 110 includes a reproduction and growth area 25, a silo area 26, and a storage area 27. The reproduction and growth area 25 includes a majority of the area of the insect rearing facility 110. In various aspects, the insect rearing facility 110 may also include one or more of a workshop, changing rooms, offices, chemical store, water tanks, milling area, chemical production area, product preparation area, grinding silos, silos to store by-product(s), areas for dispatch warehouses, etc. The insect rearing facility 110 may have alternative arrangements in other examples.

Various components of the insect rearing facility 110 are under control of one or more control units such that insect rearing tasks are fully automated, as will be described in more detail throughout this disclosure. For example, such insect rearing tasks may include supply of food to trays, supply of water to trays, distribution of food uniformly throughout the area of the trays, separation of insect excrement, collection of the excrement, collection and separation of adult larvae and moulted skins, separation of some of the adult larvae for growing adult animals for reproduction, collection of eggs, removal of adult animals after they have reproduced, and control of temperature, humidity, and/or air renewal in the environment where the trays are housed.

The insect rearing facility 110 includes valves, motors, sensors, air conditioning units, air extractors, fans, feed hoppers, conveyor belts, vacuum aspiration systems, and other like components described herein. At least some of these components are under control of the one or more control units. A control unit includes at least one processor in communication with at least one memory. The at least one processor may include a controller, a microcontroller, a logic unit, an application specific integrated circuit, or any other similar device. The at least on memory may store instructions that may be executed by the one or more processors of the control unit to perform the operations described herein. The control unit is configured to receive signals from sensors, such as the light sensors, humidity sensors, temperature sensors, weight sensors, moisture sensors, motion sensors, and/or video sensors. The control unit is programmed to effectuate insect rearing operations, as discussed herein. For instance, the control unit may be programmed to cause certain operations to be performed at predetermined times or in response to feedback from the various sensors. The control unit is also programmed to cause various operations to be performed simultaneously.

Figure 2:
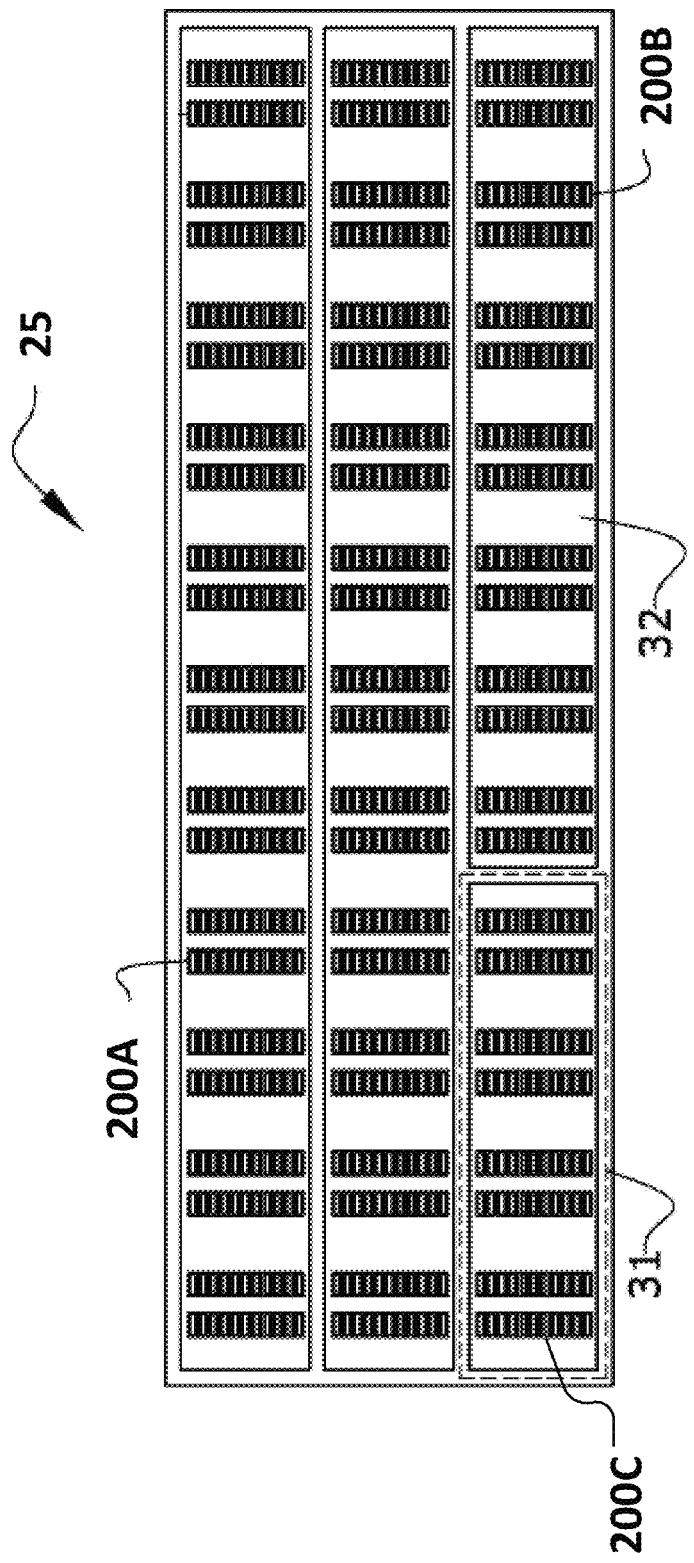
FIG. 2 illustrates a schematic of an example reproduction and growth area, according to an aspect of the present disclosure.

FIG. 2 illustrates a schematic of a plan view of the example reproduction and growth area 25 of FIG. 1, according to an example embodiment of the present disclosure. The reproduction and growth area 25 includes a plurality of modules 200A, 200B, 200C that are arranged in an ordered configuration. The modules 200A, 200B, 200C may be stacked in various heights. As will be described in more detail below, the modules 200A, 200B, 200C include sets of trays, which hold insects during the reproduction and growth processes. The reproduction and growth area 25 is divided into a reproduction area 31 and a growth area 32. The reproduction area 31 is a smaller area than the total space or volume allocated for the growth area 32 because, in reproduction, the number of laid eggs and egg density is very high. The modules 200A and 200B in the growth area 32 may be configured differently than the modules 200C in the reproduction area 31, which will be described in more detail below.

Figure 3:
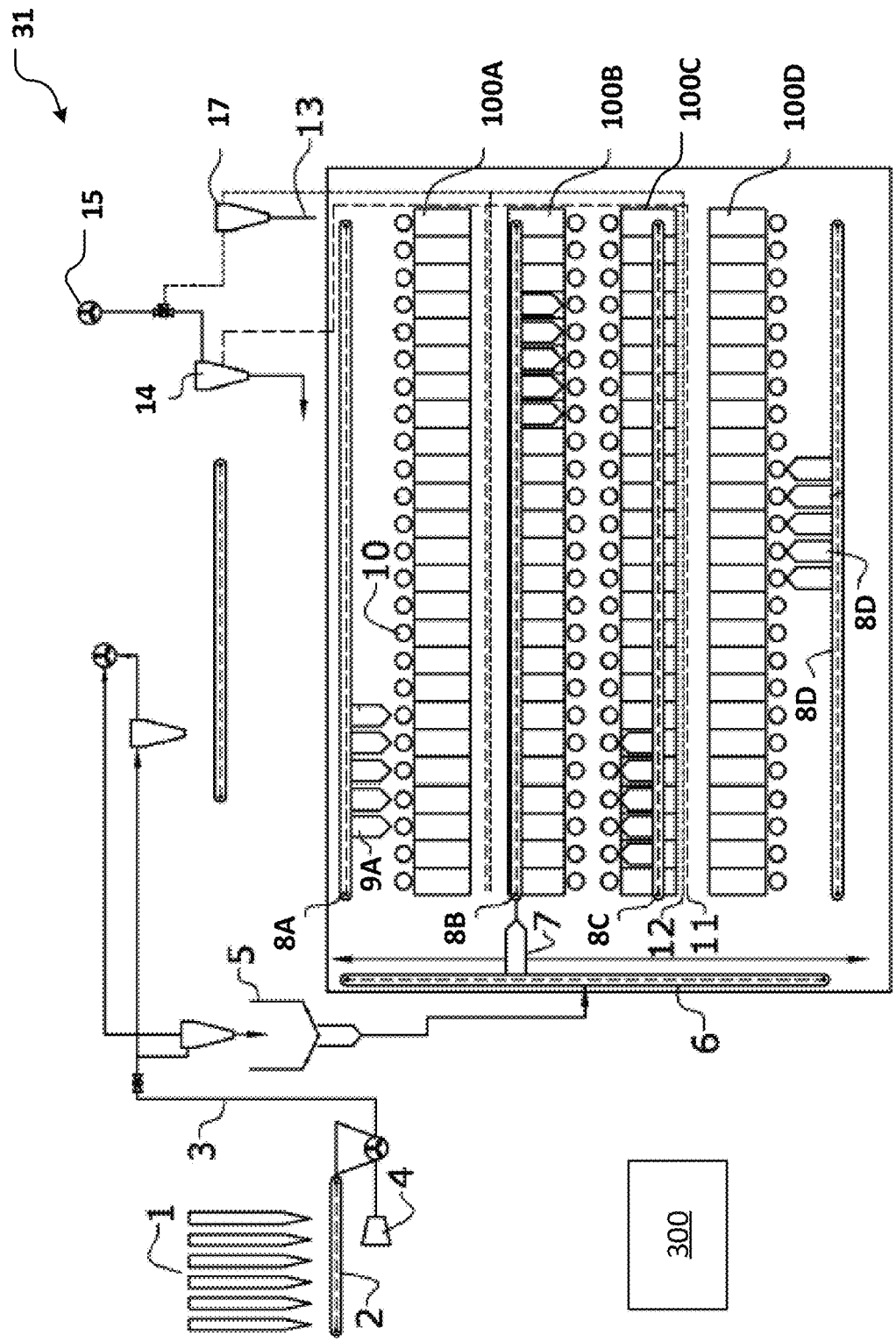
FIG. 3 illustrates an example layout of a reproduction area, according to an aspect of the present disclosure.

FIG. 3 illustrates an example layout of the reproduction area 31 of FIG. 2, according to an example embodiment of the present disclosure. The reproduction area 31 is described as having only one of various components, but it should be appreciated that the reproduction area 31 may have more than one of various described components based on the size of the insect rearing facility. Some components may also not be required or may be combined with other components. The reproduction area 31 includes a feed silo 1 that contains insect feed. The feed may include vegetable by-products including wheat bran. In other examples, the feed may include corn bran, oats, or beer yeast. In some examples, raw materials such as algae, nutrients, or supplements may be added. In various instances, the feed may be in the form of sheets, leaves, flakes, or pellets. The reproduction area 31 may also include a transport chain 2 onto which the feed silo 1 unloads insect feed. The transport chain 2 directs the feed to a distribution duct 3. A blower 4 may help transport the feed into and through the distribution duct 3 to a storage tank 5.

The reproduction area 31 also includes a primary distribution slider 6. A primary feed hopper 7 is mounted on, or otherwise connected to, the primary distribution slider 6. In various examples, the primary feed hopper 7 is a volumetric feed hopper having volumetric filling control. Feed from the storage tank 5 is fed into the primary feed hopper 7. The primary distribution slider 6 may transport the primary feed hopper 7 back-and-forth along its length. For example, the primary distribution slider 6 may be a production belt on rollers powered by a motor. As in the illustrated example, the distribution slider 6 has a length equal to the area to be covered so that it may enable transportation of the primary feed hopper 7 over the entire area.

The reproduction area 31 also includes a set of secondary distribution sliders 8A, 8B, 8C, 8D. For example, there may be one secondary distribution slider 8A, 8B, 8C, 8D for each module row 100A, 100B, 100C, 100D. The secondary distribution sliders 8A, 8B, 8C, 8D may be configured in the same manner as the primary distribution slider 6. Each of the secondary distribution sliders 8A, 8B, 8C, 8D includes one or more secondary feed hoppers 9A, 9B. 9C, 9D that are mounted on, or otherwise connected to, a respective secondary distribution slider 8A, 8B, 8C, 8D. The secondary feed hoppers 9B and 9C of the secondary distribution sliders 8B and 8C, respectively, are not shown in FIG. 3 for the sake of clarity of the figure. In various examples, the secondary feed hoppers 9A, 9B. 9C, 9D are volumetric feed hoppers having volumetric filling control. The respective secondary distribution sliders 8A, 8B, 8C, 8D may transport the respective secondary feed hoppers 9A, 9B. 9C, 9D back-and-forth along their lengths. For example, the secondary distribution sliders 8A, 8B, 8C, 8D may be production belts on rollers powered by a motor. As in the illustrated example, the secondary distribution sliders 8A, 8B, 8C, 8D have lengths equal to the length of the module rows 100A, 100B, 100C, 100D so that they may enable transportation of the secondary feed hoppers 9A, 9B. 9C, 9D to each of the respective modules.

The primary feed hopper 7 is transported back-and-forth to deliver feed to each of the secondary feed hoppers 9A, 9B. 9C, 9D mounted on each of the secondary distribution sliders 8A, 8B, 8C, 8D. For instance, the secondary distribution slider 8A may transport the secondary feed hoppers 9A the leftmost end of the secondary distribution slider 8A, and the primary distribution slider 6 may transport the primary feed hopper 7 to the topmost end of the primary distribution slider 6, so that the primary feed hopper 7 may deliver feed to the secondary feed hoppers 9A.

The reproduction area 31 also includes a plurality of feed distribution columns 10. For instance, as in the illustrated example, each module in the respective rows of modules 100A, 100B, 100C may have its own corresponding feed distribution column 10. It should be appreciated that only a single feed distribution column 10 is shown in FIG. 3 for the sake of clarity. As illustrated in FIG. 3, the secondary distribution sliders 8A, 8B, 8C, 8D are positioned on a support structure to be above the module rows 100A, 100B, 100C, 100D and the distribution columns 10. For example, the secondary distribution sliders 8B and 8C and their respective secondary feed hoppers 9B and 9C are illustrated overlapping the module rows 100B and 100C. The primary distribution slider 6 and the primary feed hopper 7 may also be positioned on the same support structure, or a similar support structure, to enable feed distribution to the secondary feed hoppers 9A, 9B. 9C, 9D.

The respective secondary distribution sliders 8A, 8B, 8C, 8D transport their respective secondary feed hoppers 9A, 9B, 9C, 9D to a respective feed distribution column 10 so that a secondary feed hopper 9A, 9B, 9C, 9D may provide feed to a particular feed distribution column 10 from above. Stated differently, each respective feed distribution column 10 may be provided with feed independently of the other feed distribution columns 10. A feed distribution column 10 may then distribute food to its respective module. The feed distribution columns 10 may form a larger gravity-based feed distribution system or network, which will be described in more detail in connection with FIGS. 9 to 11.

Also included in the reproduction area 31 is a vacuum aspiration system that is configured to retrieve and collect objects from the modules. The vacuum aspiration system includes one or more sets of aspiration arms (not illustrated), a vacuum (not illustrated), piping 11, 12, and decanters 14, 17. The vacuum is in fluid communication with the sets of aspiration arms such that, when activated, the vacuum causes objects to be aspirated into the aspiration arms and through the piping 11, 12. In an example, the vacuum may include pneumatic actuators configured to open and close vacuum suction apertures depending on whether the vacuum is activated or deactivated. The actuators are in communication with the insect rearing facility's control unit 300. The vacuum may also include limit switches for aligning the positions of the aspiration arms prior to activating the vacuum.

The aspiration arms are mobile such that they may be transported (e.g., the example path illustrated in FIG. 5) between the module rows 100A, 100B, 100C, 100D to aspirate objects from the respective modules. In some instances, the aspiration arms are a component of a mobile assembly that also includes a vacuum. A set of aspiration arms may include two arms, a first aspiration arm and a second aspiration arm, that serve different purposes. In the reproduction area 31, the first aspiration arm aspirates adult insects that have stopped being fertile, while the second aspiration arm aspirates eggs, recently hatched larvae, excrement, and feed remains.

The first aspiration arm is in fluid communication with a pipeline 11 that is in fluid communication with a decanter 14. As illustrated in FIG. 3, the pipeline 11 may include two segments that branch off between the module rows 100A and 100B and between the module rows 100C and 100D. The pipeline 11 may include a first aspiration arm in fluid communication with each branch off segment. The decanter 14 separates adult insects from the rest of the aspirated material. The decanter 14 is also in fluid communication with a duct 16 that transports the adult insects to another area of the facility for processing into feed or fertilizer. The second aspiration arm is in fluid communication with a pipeline 12 that is fluid communication with a decanter 17. As illustrated in FIG. 3, the pipeline 12 may include two branch off segments, between the module rows 100A and 100B and between the module rows 100C and 100D. The pipeline 12 may include a second aspiration arm in fluid communication with each branch off segment. The decanter 17 separates the eggs and recently hatched larvae from the rest of the aspirated material, such as the excrement and feed remains. The decanter 17 is also in fluid communication with a duct 13 that transports the eggs and recently hatched larvae to the growth area 32.

The decanters 14 and 17 may include an inertial separator configured to separate the different material based on weight. In an example, the decanters 14, 17 include an internal chamber connected to an inlet pipeline. At least one pipeline may be connected to a top or side of the internal chamber. In addition, at least one pipeline may be connected to a bottom side of the internal chamber of the decanters 14, 17. The air flow is configured such that lighter particles rise within the internal chamber and exit through the top exit pipeline(s). In contrast, heavier particles decant when the particles contact a blade (e.g., a sheet metal blade) within the internal chamber. The air flow in the decanters 14, 17 may be provided by a fan within the internal chamber or external to the chamber (e.g., fan 15) via ductwork and a vent. The speed of the air flow may be adjusted based on the contents being decanted. For example, a first speed may be used to separate larvae from waste/food/skins and a second speed may be used to separate adult insects from waste/food/eggs.

In some examples, the modules in the reproduction area 31 may include a nursery tray that includes a mesh layer with openings having a specific size to retain eggs while enabling feed and waste to pass through. In some instances, the eggs may be then be collected from the nursery trays via the vacuum system and transported to the growing area 32. In other instances, the mesh trays themselves may be inserted into the growing area 32.

Figure 4:
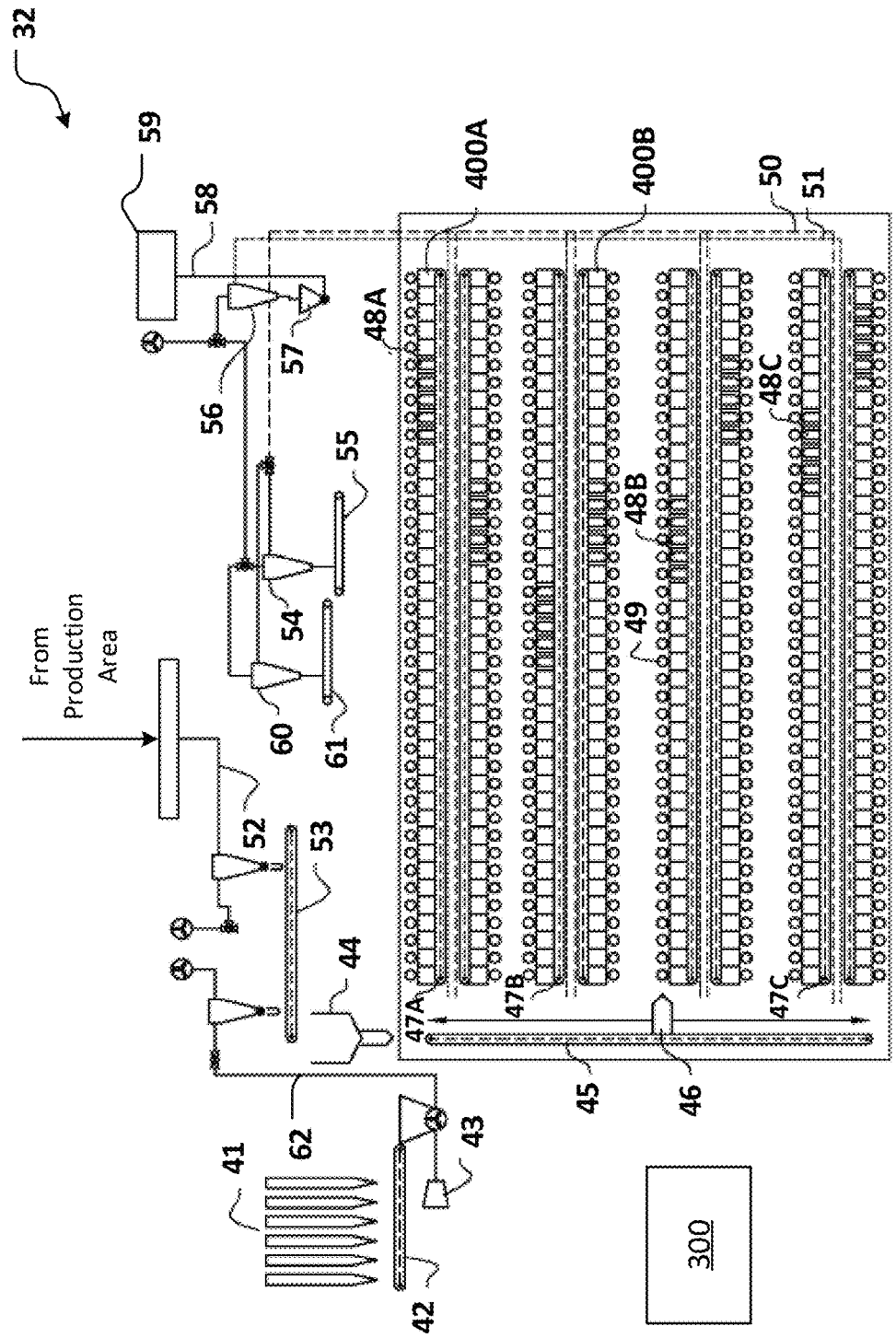
FIG. 4 illustrates an example layout of a growth area, according to an aspect of the present disclosure.

FIGS. 3 and 4 show a control unit 300. As described herein, the control unit 300 is programmed to receive sensor feedback, video, or measurement data from one or more sensors or cameras. The control unit 300 is also configured to control valves, motors, actuators, aspiration arms, decanters, etc. to provide automatic control for rearing insects. Control by the control unit 300 may be provided according to a preprogrammed routine (e.g., provide water/feed at designated times) ad/or based on data from the sensors/cameras. The control unit 300 is communicatively coupled via a wired or wireless connection to the components described herein. For brevity, these connections are not shown.

FIG. 4 illustrates an example layout of the growth area 32 of FIG. 2, according to an example embodiment of the present disclosure. The growth area 32 may be configured in accordance with the above description of the reproduction area 31, except for the differences that are highlighted in the foregoing description of the growth area 32. For instance, the growth area 32 includes a feed silo 41 that contains insect feed. The growth area 32 may also include a transport chain 42 onto which the feed silo 41 unloads insect feed. The transport chain 42 directs the feed to a distribution duct 62. A blower 43 may help transport the feed into and through the distribution duct 62 to a storage tank 44. In the growth area 32, however, the storage tank 44 may also receive eggs or recently hatched larvae (and possibly excrement or excess feed if not properly sorted) from the reproduction area 31. The eggs or recently hatched larvae may be transported through a distribution duct 52 to the storage tank 44. A transport chain 53 may direct both feed and the eggs/larvae to the storage tank 44 depending on instructions from the control unit 300. For instance, eggs/larvae may be directed to the storage tank 44 when modules are available to receive the eggs/larvae.

The growth area 32 also includes a primary distribution slider 45 and a primary feed hopper 46. The growth area 32 further includes a set of secondary distribution sliders 47A, 47B, 47C, only some of which are indicated in FIG. 4 for the sake of clarity. Each of the secondary distribution sliders 47A, 47B, 47C includes one or more secondary feed hoppers 48A, 48B, 48C, only some of which are indicated in FIG. 4 for the sake of clarity. The secondary feed hoppers 48A, 48B, 48C deliver feed to a plurality of feed distribution columns 49. The secondary distribution sliders 47A, 47B, 47C, and in some instances, the primary distribution slider 45, are positioned on a support structure that is positioned above the module rows 400A, 400B and the distribution columns 49. It should be appreciated that only a portion of the module rows 400A, 400B are indicated in FIG. 4 for sake of clarity.

Also included in the growth area 32 is a vacuum aspiration system utilized to retrieve and collect objects from the modules. The vacuum aspiration system includes one or more sets of aspiration arms (not illustrated), a vacuum (not illustrated), piping 50, 51, and decanters 54, 56, 60. The vacuum is in fluid communication with the sets of aspiration arms such that, when activated, the vacuum causes objects to be aspirated into the aspiration arms and through the piping 50, 51. In the growth area 32, the first aspiration arm aspirates developed larvae and moulted skins, while the second aspiration arm aspirates larvae excrement.

The first aspiration arm is in fluid communication with a pipeline 50 that is in fluid communication with a decanter 54 and a decanter 60. As illustrated in FIG. 4, the pipeline 50 may include multiple branch off segments. The decanter 54 separates the developed larvae from the rest of the aspirated material. The separated larvae may fall onto a conveyor 55 that transports them to an area for dehydration and crushing, or other processing. A small portion (e.g., 3% to 10%) of the separated larvae may be further separated and allowed to mature into adult insects for reproduction purposes in the reproduction area 31. The aspirated material other than the separated larvae, primarily the moulted skins, continue through the pipeline 50 to the decanter 60. The decanter 60 separates the moulted skins from the rest of the aspirated material and the skins drop onto the conveyor 61 to be transported to another area of the facility for processing.

The second aspiration arm is in fluid communication with a pipeline 51, which is in fluid communication with a decanter 56. As illustrated in FIG. 4, the pipeline 51 may include multiple branch off segments. The decanter 56 separates the larvae excrement from the rest of the aspirated material. The separated larvae excrement may be dropped into a collection hopper 57 and carried via a duct 58 to a pellet storage tank 22. The decanters 54, 56, 60 may be configured according to the above description of the decanters 14 and 17 discussed in connection with FIG. 3.

Figure 5:
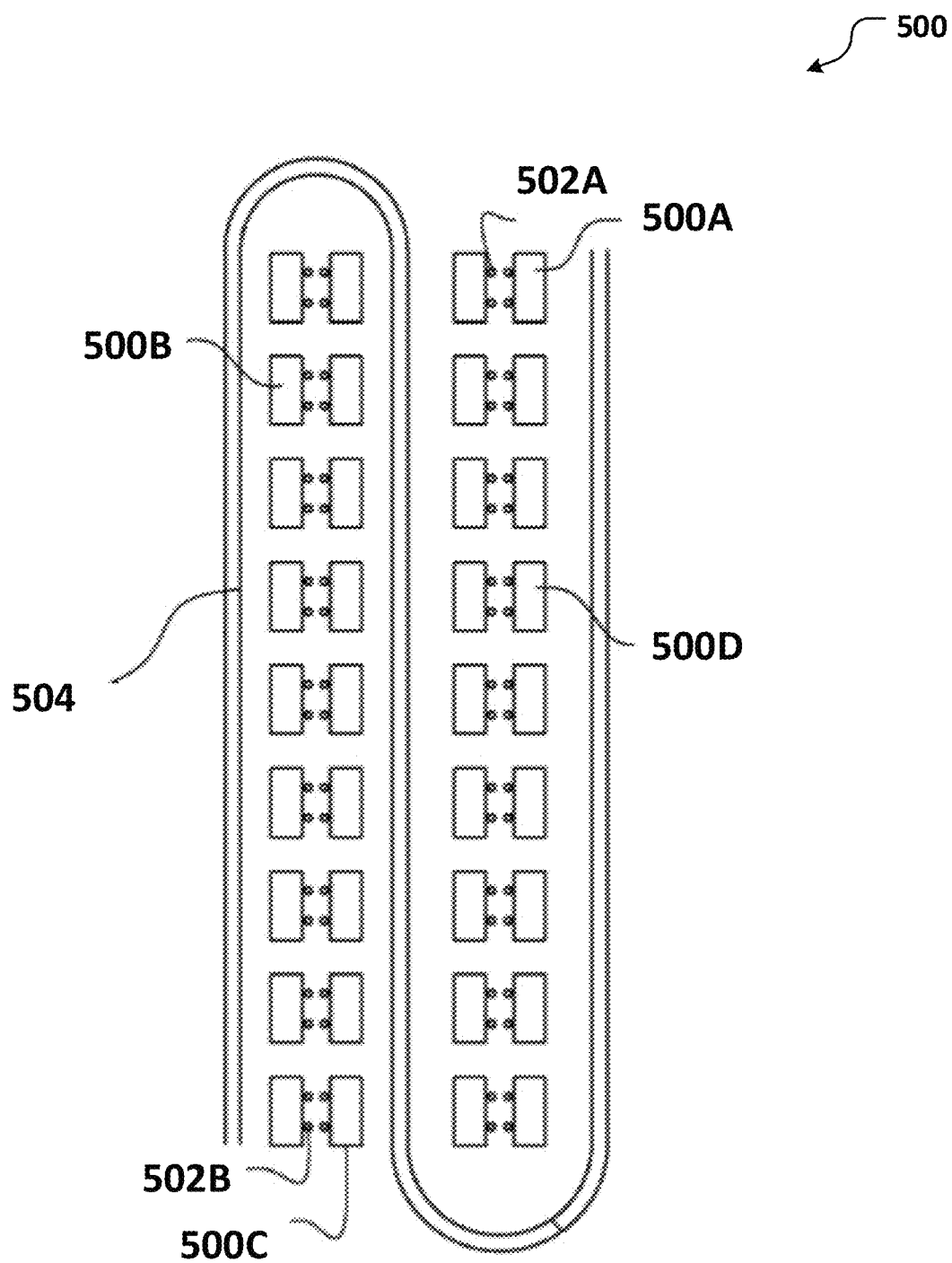
FIG. 5 illustrates an example path of guide tracks for a mobile portion of a vacuum aspiration system in a reproduction or growth area, according to an aspect of the present disclosure.

FIG. 5 illustrates an example path of guide tracks 504 for a mobile portion of a vacuum aspiration system in a reproduction or growth area 500. For example, the aspiration arms and a vacuum may be mounted on a structure including wheels that roll along the guide tracks 504. In the illustrated example, the guide tracks 504 wind around the rows of modules 500A, 500B, 500C, 500D. This may be the most efficient path for the vacuum aspiration system to reach each of the modules 500A, 500B, 500C, 500D rather than having to backtrack after reaching the end of a row. Additionally, the plurality of feed distribution columns 502A, 502B are located between the rows of modules 500A, 500B, 500C, 500D on the opposite side of the guide tracks 504. This configuration may enable easier access for the aspiration arms to the modules 500A, 500B, 500C, 500D without having the feed distribution columns 502A, 502B provide an obstruction.

Figure 6:
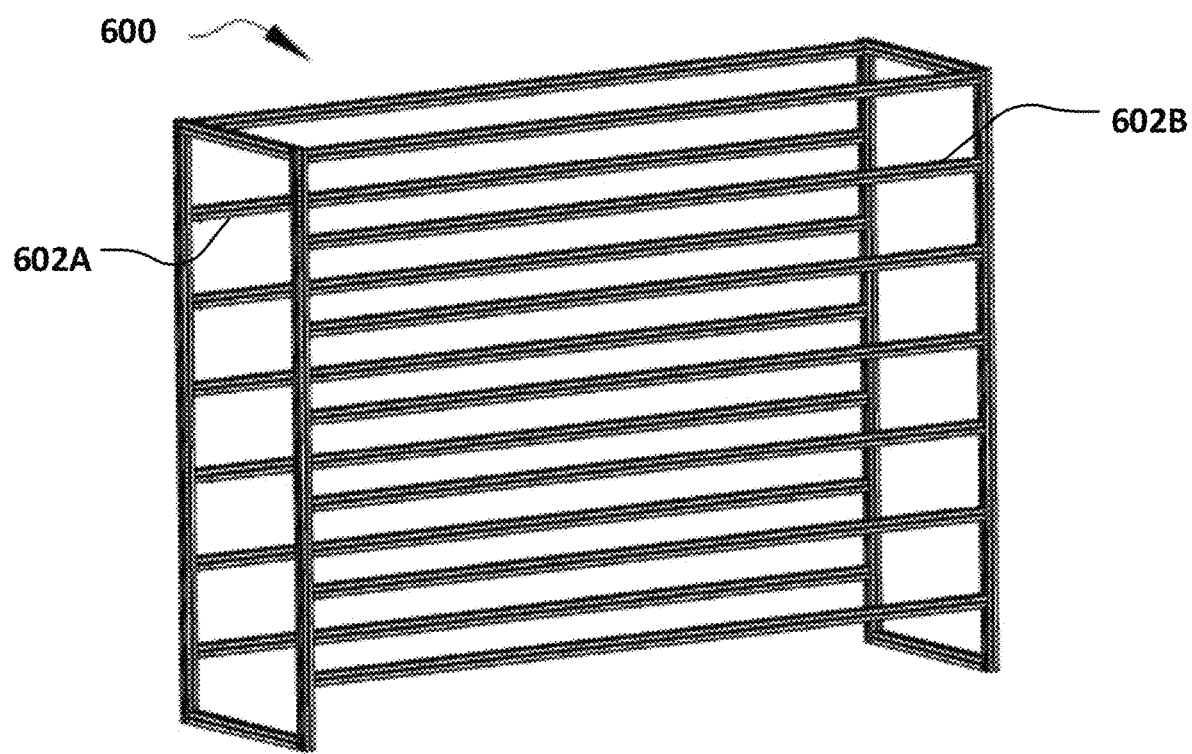
FIG. 6 illustrates an example empty module frame used for supporting trays containing insects, according to an aspect of the present disclosure.
Figure 7:
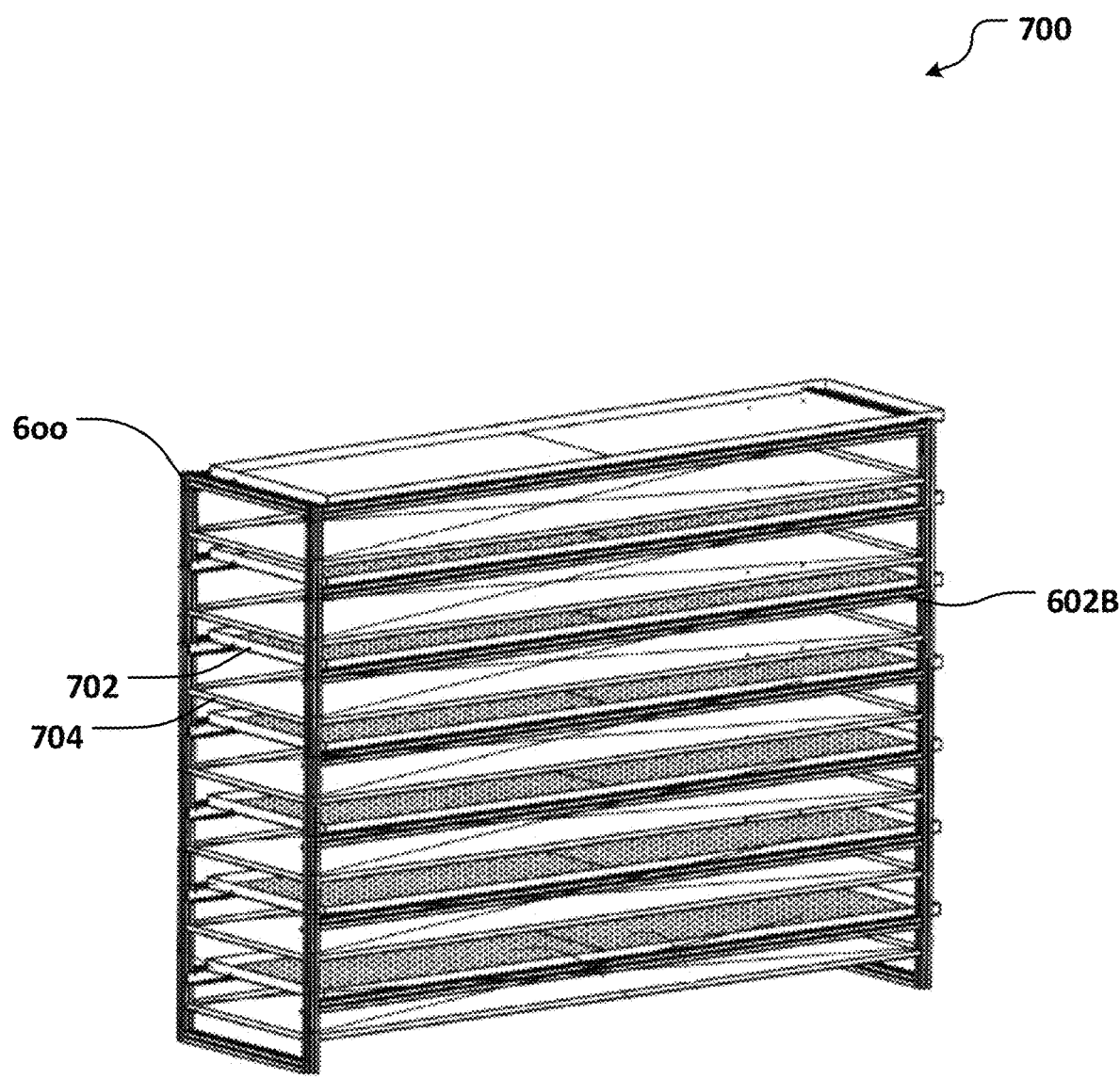
FIG. 7 illustrates an example module that includes a plurality of sets of trays that include a mobile tray and a fixed tray, according to an aspect of the present disclosure.

Each individual module, which have only been described generally in the preceding description, is now be described in more detail. FIG. 6 illustrates an example empty module frame 60 used for supporting trays containing insects. The module frame 600 includes a plurality of guide rails 602A, 602B that support the ends of the trays. The guide rails 602A, 602B separate the various rows of the module frame 600 such that the module frame 600 may support multiple rows of trays. FIG. 7 illustrates an example module 700 that includes a plurality of sets of trays that include a mobile tray 702 (e.g., an upper tray) and a fixed tray 704 (e.g., a lower tray). The mobile trays 702 are positioned above each of the fixed trays 704 in each set of trays. The mobile trays 702 are configured to contain insects, whereas the fixed trays are configured to collect products to be extracted, for instance, that fall through perforations in the mobile trays 702.

In certain aspects, the fixed trays 704 are connected to the module frame 600 such that they are not removable from the module frame 600. In other aspects, the fixed trays 704 may be supported by guide rails 602, and are physically removable from the module frame 600, though they remain positioned on the module frame 600 during farming operations as described below. The mobile trays 702 are movable with respect to the module frame 600. The mobility of the mobile trays 702 may help make it easier to provide feed or water to the mobile trays 702, or to introduce insects to the mobile tray 702. In certain instances, the mobile trays 702 are entirely separate from the module frame 600. In such instances, the mobile trays 702 may have a configuration that enables easier movement of the mobile trays 702. For instance, the mobile trays 702 may have rollers on the bottoms of the mobile trays 702.

In other instances, the mobile trays 702 may be attached to the module frame 600 such that an actuator may move the mobile trays 702 relative to the module frame 600. For example, the mobile trays 702 may be on rails and an actuator arm may extend the mobile trays 702 away from the module frame 600. In another example, an actuator may agitate or shake a respective mobile tray 702 by moving it back and forth in a quick, repetitive manner. The agitating or shaking may help evenly distribute the insects and/or food on a tray. The agitating or shaking may also cause waste products (or eggs in the reproduction area 31) to fall through a mesh (or openings) in a base of the try 702 to an underlying fixed tray 704. The actuators of the mobile trays 702 are in communication with the control unit 300.

Figure 8A:
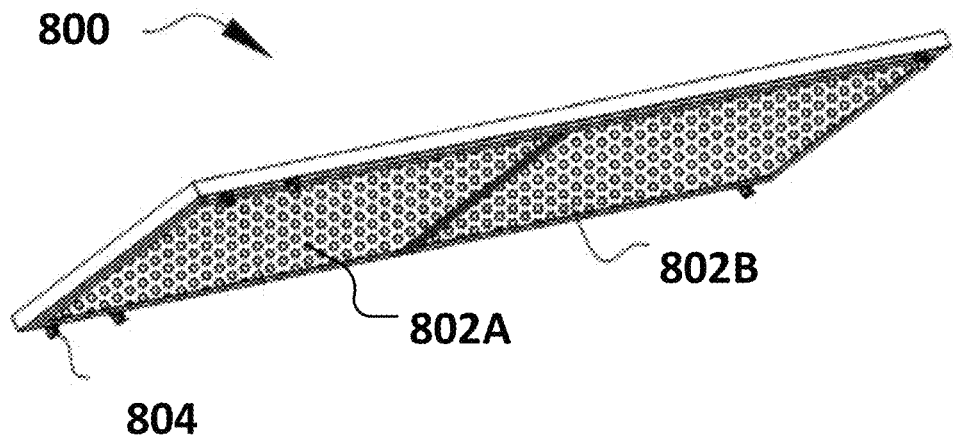
FIGS. 8A and 8B illustrate an example mobile tray, according to an aspect of the present disclosure.
Figure 8B:
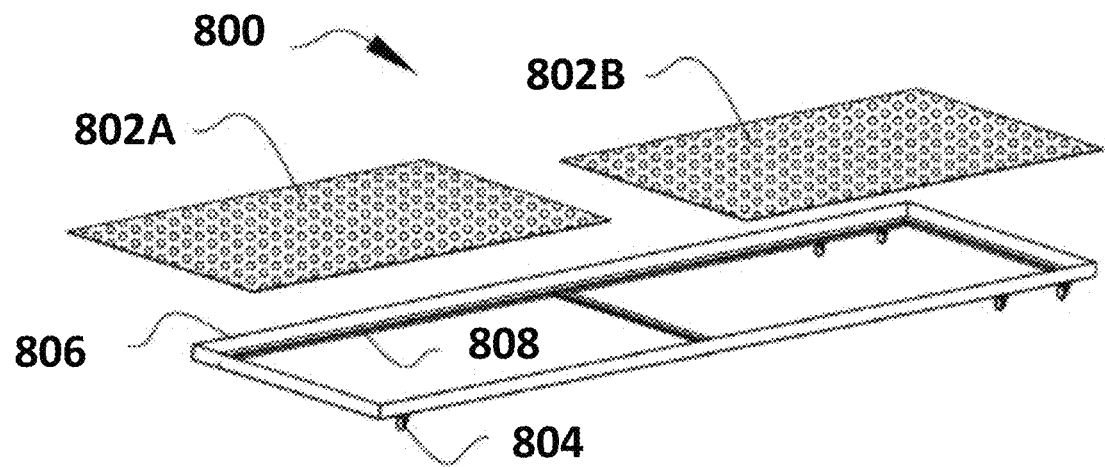

FIGS. 8A and 8B illustrate an example mobile tray 800. In various aspects, a mobile tray 800 includes a frame 806 and one or more perforated sieves 802A, 802B. The frame 806 may have a support lip 808 on its interior. The mobile tray 800 may include a plurality of rollers 804, as described above. The one or more perforated sieves 802A, 802B may be positioned within the frame 806 on the support lip 808. In other examples, the mobile tray 800 may be a single component rather than the multiple components in the illustrated example. Additionally, in the illustrated example, the mobile tray 800 includes two separate perforated sieves 802A and 802B, though in other examples the mobile tray 800 may include a single perforated sieve or more than two perforated sieves.

The one or more perforated sieves 802A, 802B of the mobile tray 800 include perforations or apertures having a diameter that depends on the intended use of a respective mobile tray 800. Modules of the present disclosure may be either a reproduction module or a growth module. Reproduction modules are configured for breeding purposes and primarily include adult insects in their mobile trays. Therefore, in reproduction modules, the mobile tray 800 perforations have a diameter (e.g., 2 millimeters ("mm")) that is sufficient for laid eggs to fall through the perforations and collect on a fixed tray beneath the mobile tray 800. In some embodiments, the mobile tray 800 (e.g., upper tray) may have a solid opaque base instead of perforations. Growth modules are configured for larvae growth from hatching of the eggs until the nymph stage, and primarily include larvae in their mobile trays. Therefore, in growth modules, the mobile tray 800 perforations have a diameter (e.g., 1 mm, 0.5 mm, 0.1 mm, etc.), which is sufficient for larvae excrement to fall through the perforations and collect on a fixed tray beneath the mobile tray 800. Larvae that come into contact with excrement may become sick, thus necessitating removal of the excrement. It should be appreciated that the perforation diameters of the reproduction module mobile trays and the growth module mobile trays may vary based on the insect species that the modules that are utilized for farming. For instance, some insects are larger than others and thus may have larger eggs and/or larger excrement, which requires larger diameter perforations.

Figure 9:
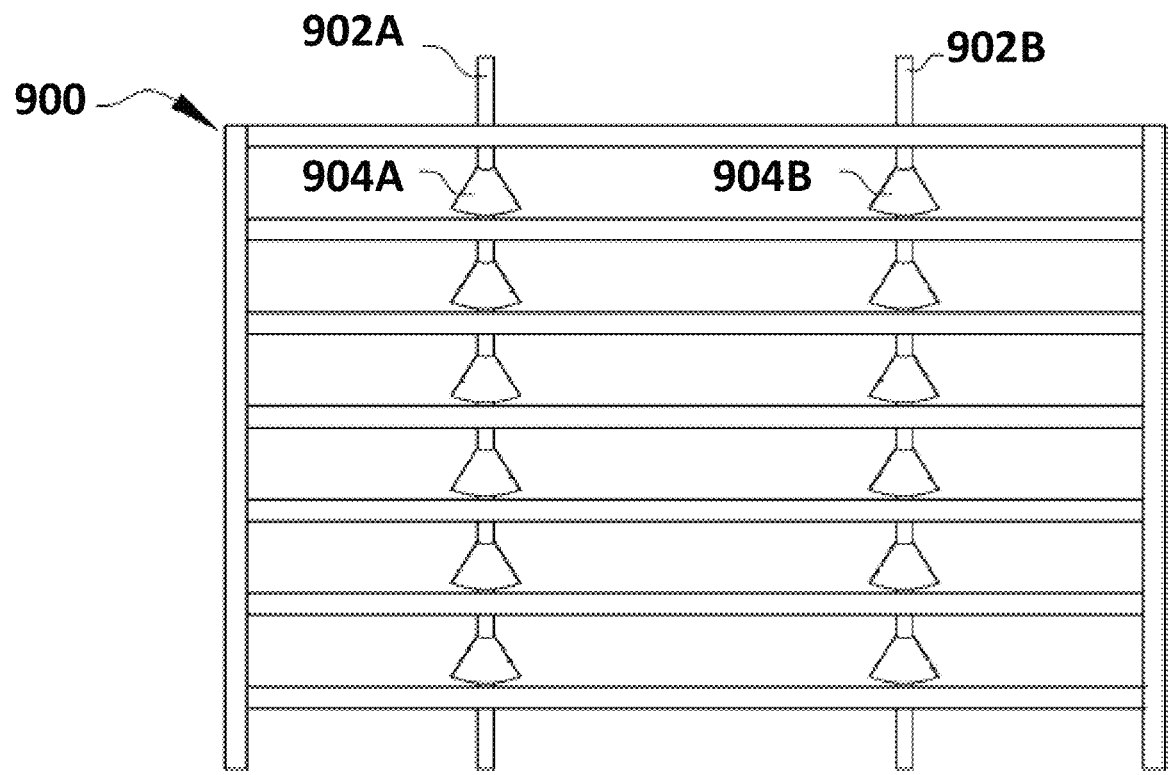
FIG. 9 illustrates an example module including a feed distribution system, according to an aspect of the present disclosure.
Figure 10:
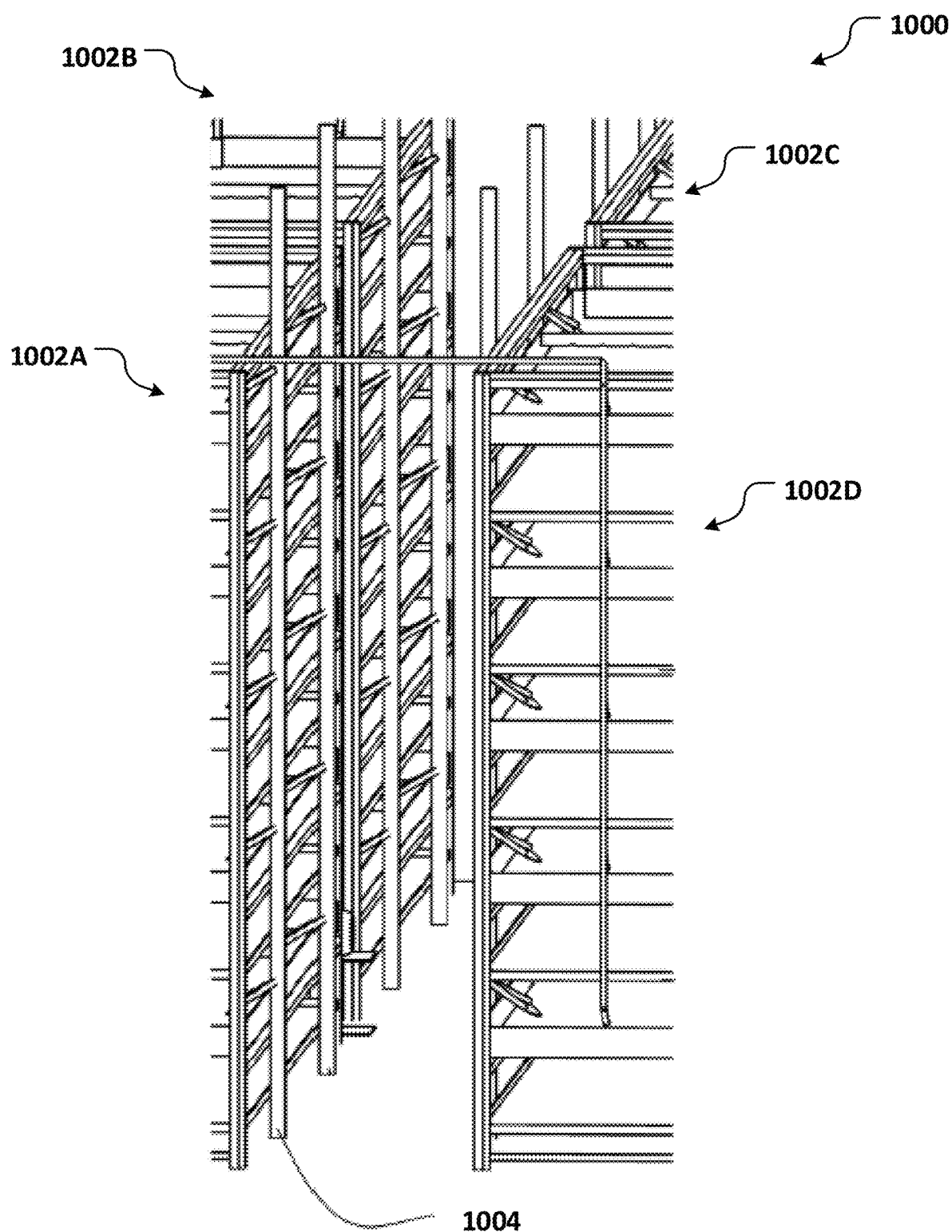
FIG. 10 illustrates multiple feed distribution systems of multiple modules that form a feed distribution network, according to an aspect of the present disclosure.

As mentioned above, the previously described feed distribution columns may form a feed distribution system. FIG. 9 illustrates an example module 900 including a feed distribution system. The feed distribution system includes a feed distribution column 902A and a feed distribution column 902B. In other examples, the module 900 may include additional feed distribution columns in the feed distribution system. The feed distribution columns 902A, 902B each include a plurality of distribution blades 904, one distribution blade 904 for each row in the module. This configuration enables the feed distribution system to distribute food to each of the trays that require feed. FIG. 10 illustrates multiple feed distribution systems of multiple modules 1002A, 1002B, 1002C, 1002D that form a feed distribution network. In the illustrated example, each of the feed distribution systems includes two feed distribution columns 1004 (shown as column 902 in FIG. 9, column 10 in FIG. 3, and column 49 in FIG. 4).

Figure 11:
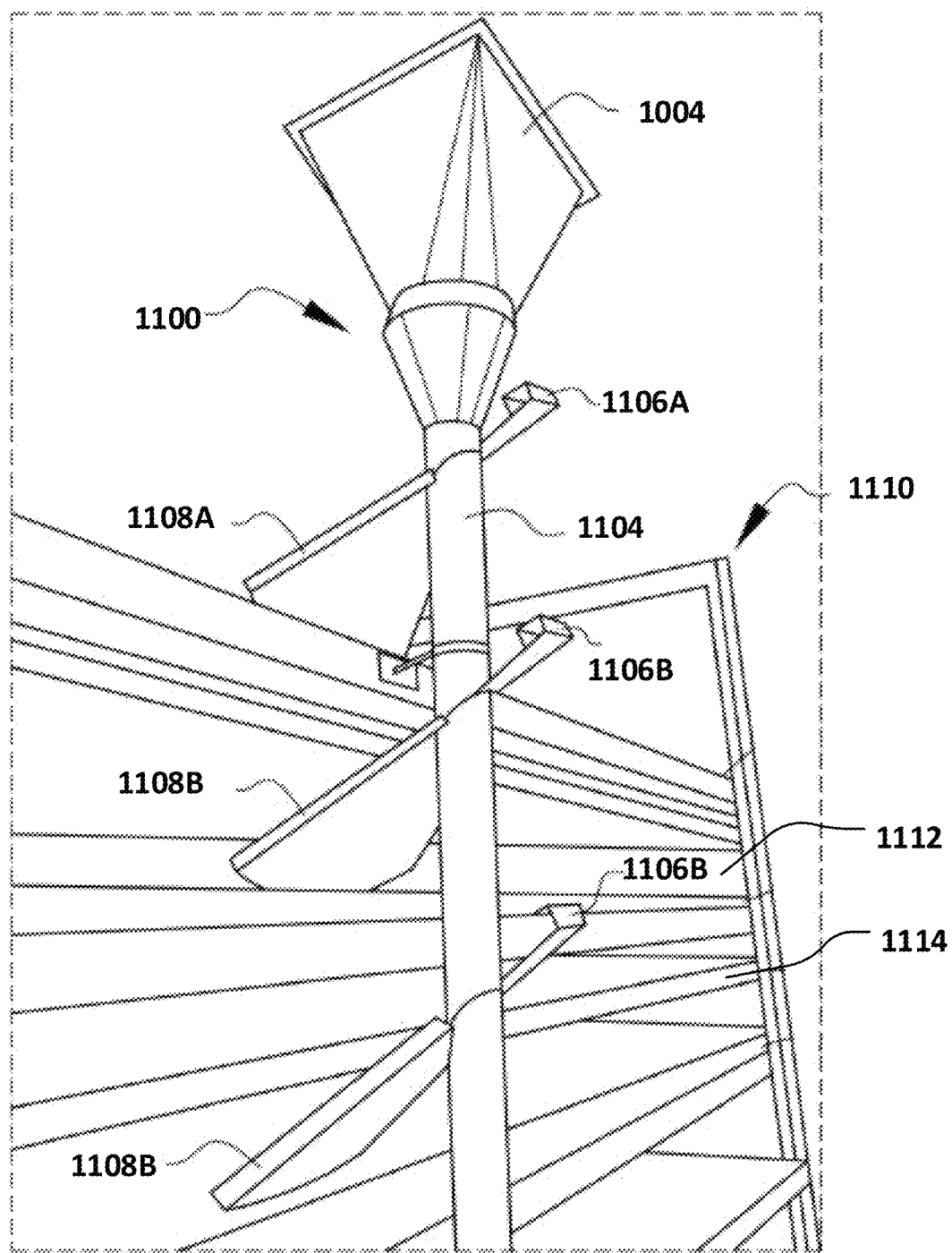
FIG. 11 illustrates a magnified view of an example gravity-based feed distribution column, according to an aspect of the present disclosure.

FIG. 11 illustrates a magnified view of an example gravity-based feed distribution column 1100, according to an example embodiment of the present disclosure. The feed distribution column 1100 includes a vertical distribution duct 1104. An upper end of the vertical distribution duct 1104 includes a hopper 1102. The secondary feed hoppers described above may distribute feed into the hopper 1102. The hopper 1102 is configured to measure an amount of feed to supply per each mobile tray 1112. For example, the hopper 1102 may measure such an amount of feed by weight or by volume, which may be communicated to the control unit 300 disclosed herein. The feed distribution column 1100 also includes a plurality of distribution blades 1108A, 1108B, 1108C that are each positioned over a mobile tray 1112. The mobile trays 1112 are illustrated above fixed trays 1114. The distribution blades 1108A, 1108B, 1108C are angled downward such that gravity forces feed from the vertical distribution duct 1104 down the distribution blades 1108A, 1108B, 1108C and into respective mobile trays 1112.

The feed distribution column 1100 also includes a series of valves 1106A, 1106B, 1106C that allow or block passage through the vertical distribution duct 1104 to the distribution blades 1108A, 1108B, 1108C. For example, when feed is to be supplied to the mobile tray 1112 via the distribution blade 1108B, the valve 1106A arranged above the mobile tray 1112 is opened and the valve 1106B is closed (via instruction from the control unit 300). Therefore, feed from the hopper 1102 may travel down the vertical distribution duct 1104, through the valve 1106A, down the distribution blade 1108B, and into the mobile tray 1112. In another example, if feed then needs to be supplied via the distribution blade 1108C (as determined by the control unit 300), the valve 1108B is opened and the valve 1108C is closed so that feed from the hopper 1102 may travel down the vertical distribution duct 1104, through the valves 1106A and 1106B, down the distribution blade 1108C, and into the mobile tray.

In various instances, the valves 1106A, 1106B, 1106C are in wireless or wired communication with the control unit 300 of the insect rearing facility. For example, the valves 1106A, 1106B, 1106C may be electrically actuated solenoid valves or pneumatically actuated valves. The control unit 300 controls which valves 1106A, 1106B, 1106C are open and which are closed to control feed distribution. The control unit 300 may also control how much feed is provided to the hopper 1102, based on weight and/or volume. The determination as to the amount of feed needed may correspond to weight or other data received from one or more sensors. Additionally or alternatively, the control unit 300 may be programmed to effectuate feeding at predetermined times.

Figure 12:
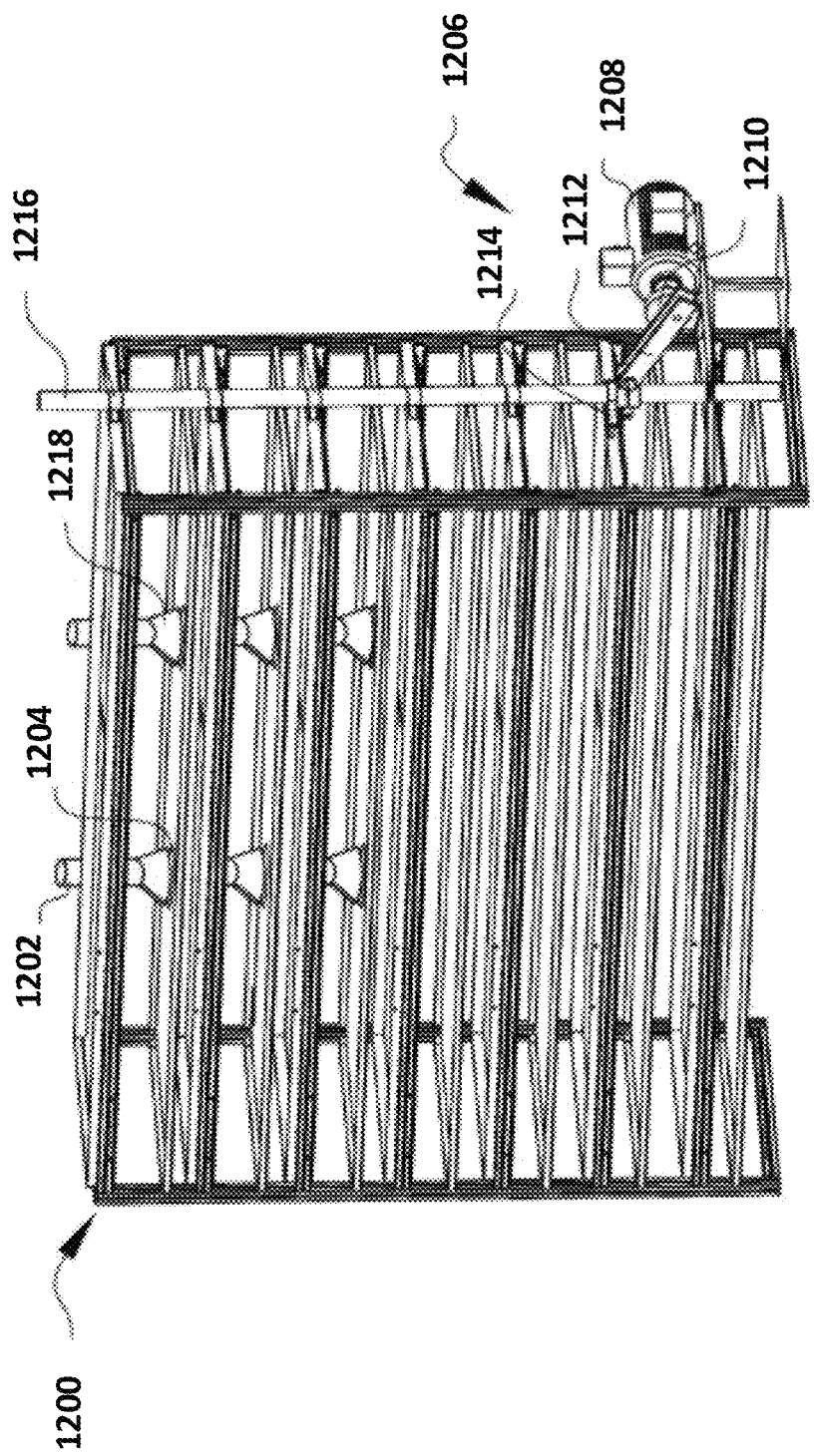
FIG. 12 illustrates an example module in which feed from a feed distribution column is piled up at the foot of distribution blades, according to an aspect of the present disclosure.

In many instances, the above-described gravity-based feed distribution column results in feed piled up at the foot of the distribution blades. For instance, FIG. 12 illustrates an example module 1200 in which feed 1204 from a feed distribution column 1202 is piled up at the foot of distribution blades 1218. It is desirable, however, for the feed to be evenly dispersed about a mobile tray. Accordingly, the example module 1200 is equipped with an agitation unit 1206 (e.g., an actuator) for agitating or shaking the mobile trays of the module 1200 to evenly disperse feed provided to the mobile trays. The agitation unit 1206 may include a motor 1208 associated with an eccentric 1210. A cam 1212 may be mounted on the eccentric 1210. The cam 1212 may connect to a transmission column 1216 at a connection 1214. The transmission column 1216 is connected to each of the mobile trays of the module 1200. The agitation unit 1206 may therefore agitate or shake each of the mobile trays of the module 1200 by agitating or shaking the transmission column 1216.

The inventors have observed that agitating or shaking the mobile trays causes feed to accumulate at the end of the mobile trays opposite the connection 1214 to the cam 1212. To compensate for this feed accumulation effect, the mobile trays may have a slight inclination or slope toward the connection 1214. In some embodiments, the control unit 300 is configured to cause the feed distribution column 1202 to agitate or shake the transmission column 1216 after causing feed to be dispensed.

Figure 18:
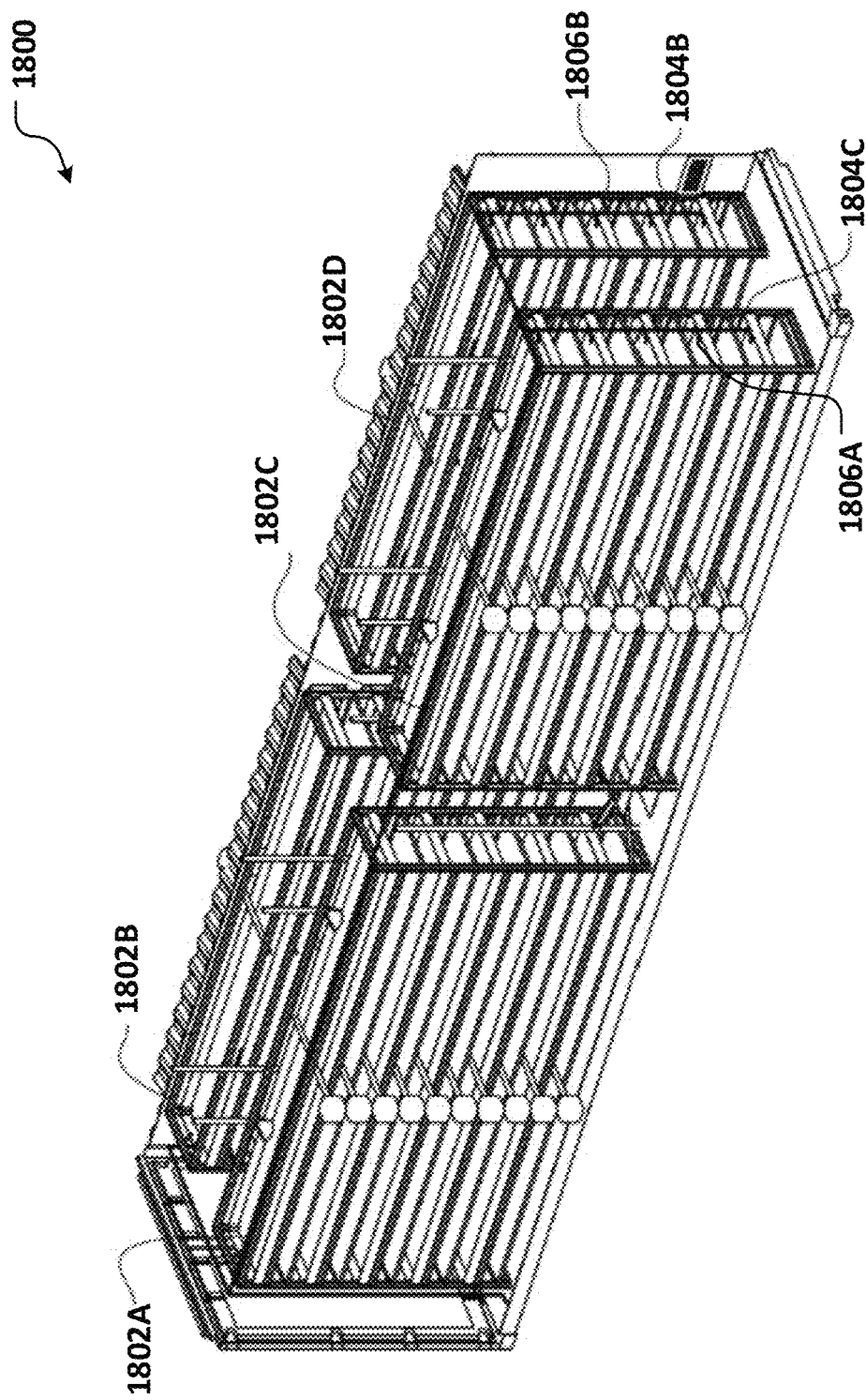
FIG. 18 illustrates a water distribution network of an example container, according to an aspect of the present disclosure.

In various aspects of the present disclosure, the provided modules may also include a water distribution system that together form a water distribution network (e.g., FIG. 18). An example water distribution network may include tubing that is structured to be positioned along the length of the modules, with a vertical tube for each module. A secondary tube may extend from the vertical tube for each mobile tray. Water may exit from the secondary tube to supply water to the mobile tray. This water supply takes place over a hygroscopic material, not edible by either the larvae or by adult insects. In various examples, the water distribution network also includes valves to control which particular secondary tubes water is provided from. In such examples, the valves may be in communication with the control unit 300. For instance, the valves may be electrically actuated solenoid valves or pneumatically actuated valves. In some embodiments, the control unit 300 may cause water to be dispensed based on sensor measurements by a moisture sensor and/or a humidity sensor. In other embodiments, the control unit 300 may dispense water at predetermined times. In some embodiments, the water distribution network may be replaced by conveyors, belt, or other mechanisms that provide vegetables, such as carrots. The vegetables contain water, which is obtained by the larvae and/or adult insects.

Figure 13:
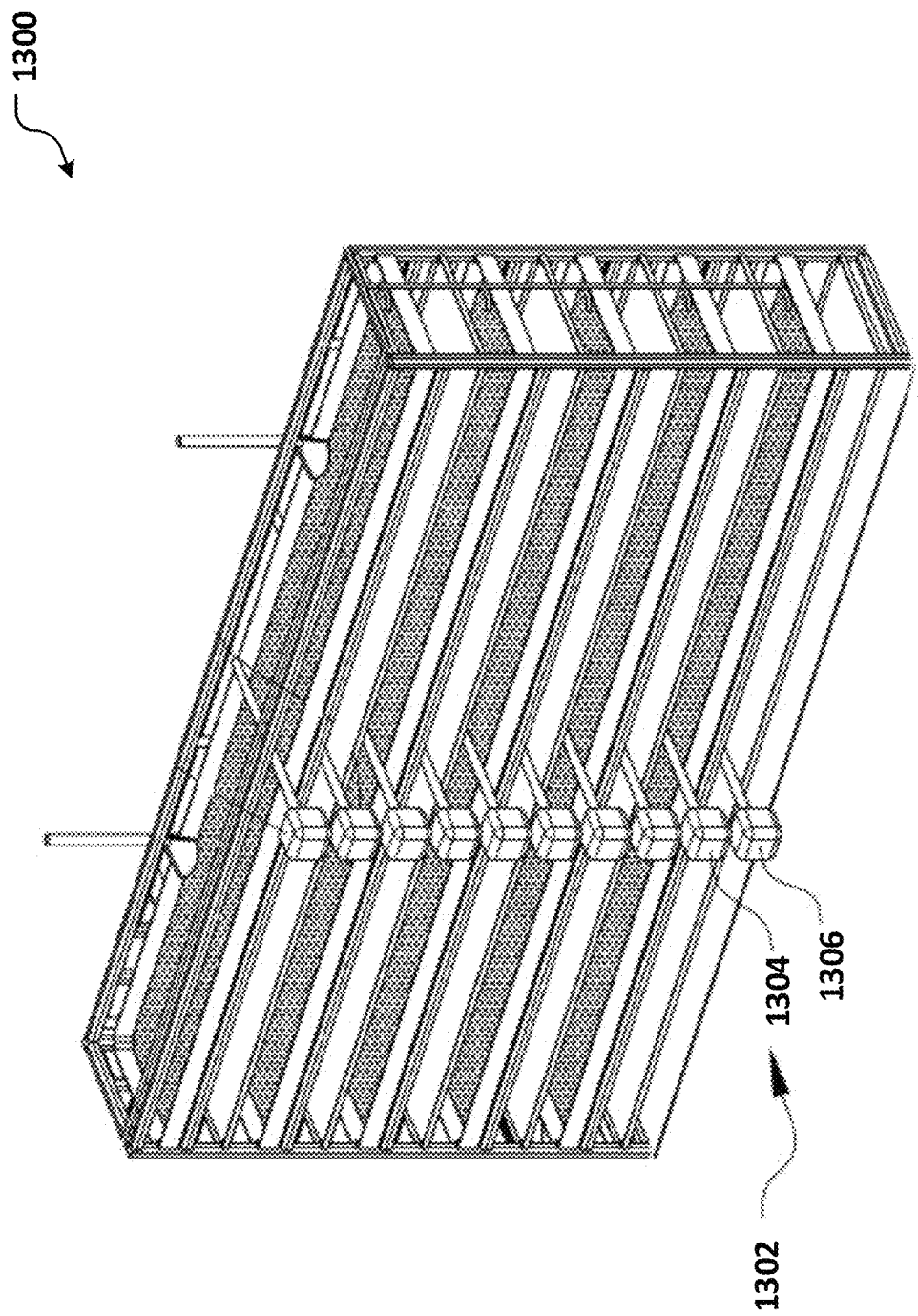
FIG. 13 illustrates an example module showing sets of aspiration arms of the vacuum aspiration system positioned within the module, according to an aspect of the present disclosure.

FIG. 13 illustrates an example module 1300 showing sets of aspiration arms of the vacuum aspiration system 1302 positioned within the module 1300, according to an example embodiment of the present disclosure. In an example, the vacuum aspiration system 1302 may include a set of a first aspiration arm 1304 and a second aspiration arm 1306 for each set of mobile trays and fixed trays of the module 1300. The first aspiration arms 1304 may collect objects, as described above, from the mobile trays. The second aspiration arms 1306 may collect objects, as described above, from the fixed trays. In at least one example, to collect the objects form the trays, both the first aspiration arm 1304 and the second aspiration arm 1306 of each set are positioned transversely to the long side of a tray, and both the first aspiration arm 1304 and the second aspiration arm 1306 of each set are transported along the entire length of the long side of the trays. Control of the aspiration arms 1304 and 1306 may be provided by the control unit 300. Aspiration may occur at predetermined times and/or based on measurements from weight sensors, movement sensors, etc.

FIG. 14A illustrates a schematic of the components of an example aspiration arm 1400. The description of the aspiration arm 1400 applies equally to both the first and second aspiration arms described in the present disclosure. The example aspiration arm 1400 includes a tube 1402 that is fluid communication on one of its ends with a vacuum or other suction source. The end 1404 of the tube 1402 is closed. The aspiration arm 1400 may also include adjustable support profiles 1406A, 1406B. The support profiles 1406A, 1406B may rest on the edges of a mobile or fixed tray as the aspiration arm 1400 is transported along the length of the trays. The support profiles 1406A, 1406B may be configured such that the transportation of the aspiration arm 1400 is made easier, such as the support profiles 1406A, 1406B being constructed of a material that reduces friction.

The tube 1402 may also be coupled to an aspiration nozzle 1410. Between the tube 1402 and the aspiration nozzle 1410 are multiple longitudinal slots 1408A, 1408B that enable suction through the aspiration nozzle 1410. FIG. 14B illustrates a cross-sectional schematic of the example aspiration arm 1400 showing the longitudinal slots 1408A, 1408B. Additionally, FIG. 14C illustrates a cross-sectional schematic of the example aspiration arm 1400 showing the construction of the tube 1402 with respect to the aspiration nozzle 1410. As illustrated, the tube 1402 may have a circular cross-section whereas the aspiration nozzle 1410 may flare out to a flat end. FIG. 14C also illustrates an open space between the tube 1402 and the aspiration nozzle 1410, denoted as the longitudinal slot 1408A. It should be appreciated that if the cross-section of FIG. 14C were to be between the longitudinal slots 1408A and 1408B, the interior of the tube 1402 would not connect to the interior of the aspiration nozzle 1410.

Figure 15:
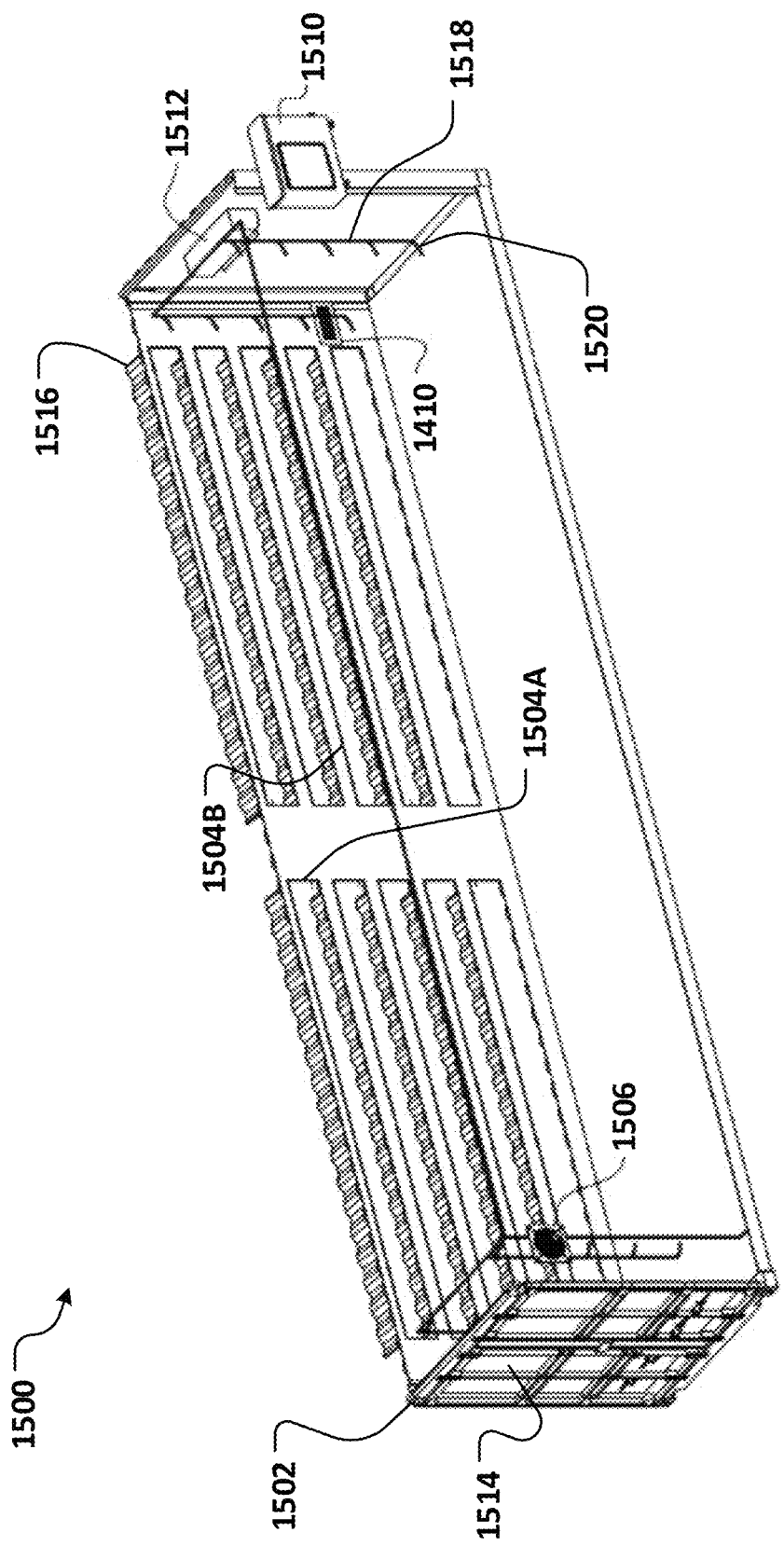
FIG. 15 illustrates an example container, according to an aspect of the present disclosure.

In various aspects of the present disclosure, most or all of the above-described components may be incorporated into an insect rearing container that autonomously regulates the insect rearing environment as well as feed and water distribution and other maintenance activities. The container may be transportable from one location to another to provide mobility to an insect rearing operation. FIG. 15 illustrates an example container 1500, according to an aspect of the present disclosure. In various instances, such as the illustrated example, the frame 1502 of the container 1500 may have a rectangular prismatic shape. In at least one particular example, the frame 1502 of the container 1500 may be, or may be configured similar to, an intermodal ISO-standard shipping container. Such a configuration enables the container 1500 to be transported by boat, train, etc. according to standard shipping procedures. In various examples, the container 1500 may be configured to house four modules, though in other examples the container 1500 may be configured to house more or less modules. In some instances, the container 1500 may hold both reproduction modules and growth modules (i.e., a reproduction area and a growth area). In other instances, a container 1500 may include solely reproduction modules or solely growth modules.

In some instances, the container 1500 may include one or more doors 1514 to allow access into the container 1500. For example, maintenance operations may occasionally require a human worker to enter the container 1500 to access various components in the interior of the container 1500. The example container 1500 includes one or more columns of openings 1504A, 1504B. The openings 1504A, 1504B are positioned corresponding to the rows of the modules positioned within the container 1500. The length of the openings 1504A, 1504B may correspond with the length of a respective module. The container 1500 also includes a hatch 1516 that may be open and closed for each opening 1504A, 1504B to provide access to the openings 1504A, 1504B. The hatches 1516 may be opened or closed manually or automatically via a motor or other actuation mechanism. Additionally, the hatches 1516 may be opened or closed all at once, or independently of each other. Each of the hatches 1516 may be typically closed to help regulate the environment within the container 1500. In certain instances, however, the hatches 1516 are opened to provide access to the modules, and in particular, to the trays on the modules. For instance, the hatches 1516 may be opened to enable aspiration arms of a vacuum aspiration system to access the trays (e.g., FIG. 16).

The container 1500 may also include an air extractor 1506, such as an air extraction fan, that extracts air from within the container 1500 and directs it outside of the container. The container 1500 also includes at least one ventilation grille 1508 to allow air to enter the container 1500. The air extractor 1506 and the ventilation grille 1508 help with air circulation within the container 1500. The container 1500 also includes at least one air conditioning unit configured for conditioning the incoming air with respect to humidity, temperature (e.g., heating or cooling), and/or ventilation. In various instances, the air conditioning unit may operate with at least one internal conditioning unit 1512 for impulsion of previously conditioned air.

FIG. 15 additionally illustrates a portion of a water distribution network. In particular the container 1500 is shown having multiple vertical tubes 1518 and multiple secondary tubes 1520 branching off of the vertical tubes 1518. A water distribution network such as the one partially illustrated in the container 1500 will be described in more detail below.

The container 1500 additionally includes a variety of sensors for detecting various conditions within the container 1500. For example, the container 1500 may include light sensors, humidity sensors, temperature sensors, weight sensors, moisture sensors, motion sensors, gas sensors, and/or video sensors. The gas sensors may be used to detect concentrations of certain gases indicative of larva growth or egg laying (or ensure certain concentrations of gases do not exceed a threshold). The gas sensors may detect, for example, $CO_2$, $CH_4$, $NH_3$, etc. The light sensors are configured to detect a level of light in the container 1500. The humidity sensors are configured to detect a level of humidity within the container 1500. The temperature sensors are configured to detect a temperature within the container 1500. The weight sensors, in an example, may be positioned underneath mobile trays and/or fixed trays to detect a content weight of a respective tray. The moisture sensors are configured to detect a moisture level in a tray. For instance, the moisture level may help determine whether water should be provided to the tray. The motion sensors are configured, in an example, to detect when insect eggs have hatched. The video sensors are configured, in an example, to detect when insect eggs have hatched. A person having skill in the art will appreciate that the sensors may be used for a variety of purposes throughout the insect rearing operations, and that other sensors beyond the examples sensors may be utilized.

The container 1500 also includes a control unit 1510 programmed to control the various operations in the container 1500. The control unit 1510 may be in communication with, or under the control of, one or more control units of the insect rearing facility (e.g., the insect rearing facility 110) in which the container 1500 is stored. The valves, motors, sensors, air conditioning units, air extractors, fans, feed hoppers, and other like components of the container 1500 described herein are under control of the control unit 1510 of the container 1500. The control unit 1510 includes at least one processor in communication with at least one memory.

The control unit 1510 is configured to receive signals from the sensors, such as the light sensors, humidity sensors, temperature sensors, weight sensors, moisture sensors, motion sensors, and/or video sensors. The control unit 1510 is programmed to effectuate insect rearing operations as discussed herein. For instance, the control unit 1510 may be programmed to cause certain operations to be performed at predetermined times or in response to feedback from the various sensors. The control unit 1510 is also programmed to cause various operations to be performed simultaneously. For example, such insect rearing tasks may include supply of food to trays, supply of water to trays, distribution of food uniformly throughout the area of the trays, separation of insect excrement, collection of the excrement, collection and separation of adult larvae and moulted skins, separation of some of the adult larvae for growing adult animals for reproduction, collection of eggs, removal of adult animals after they have reproduced, and control of temperature, humidity, and/or air renewal in the container 1500.

Figure 16:
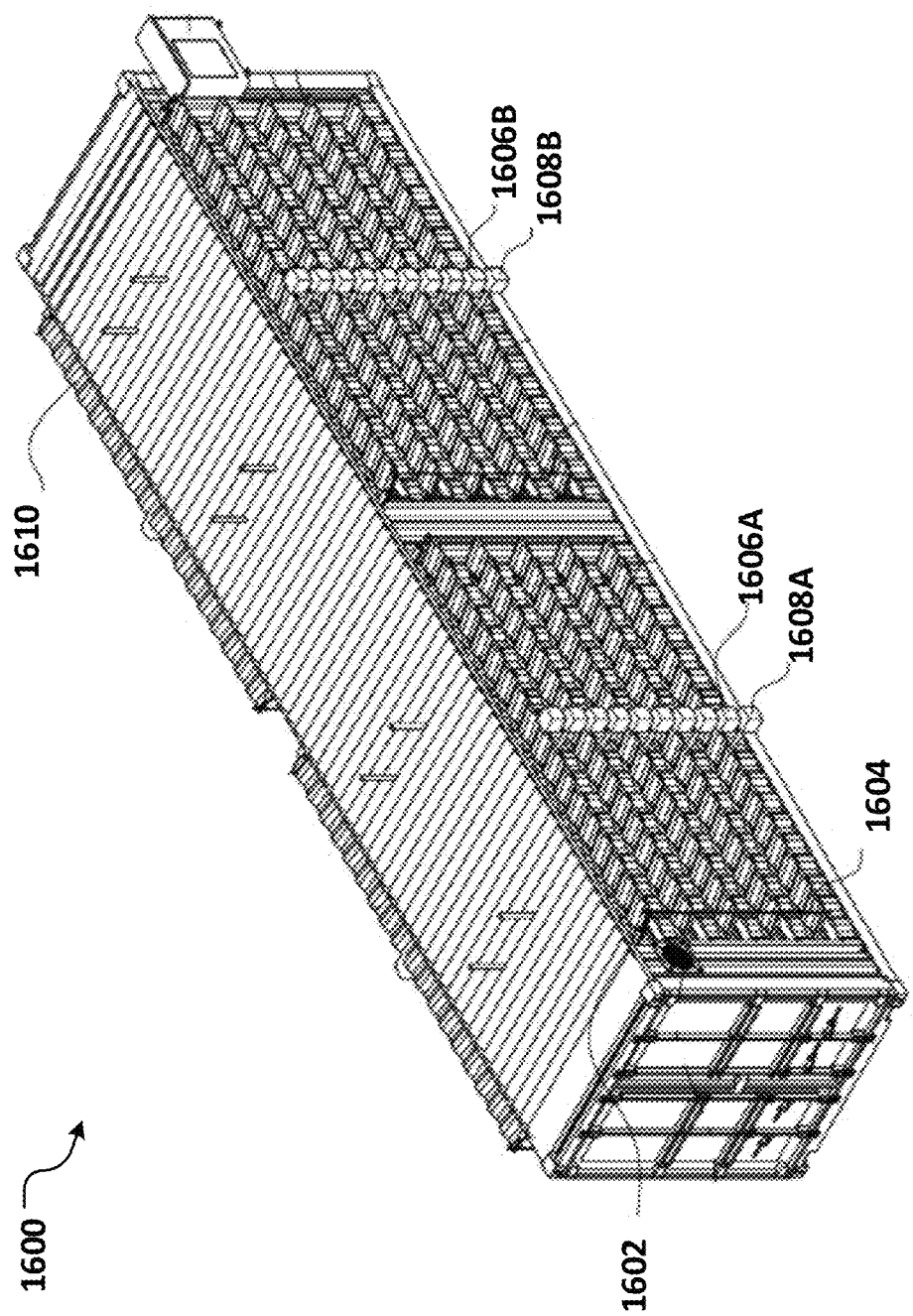
FIG. 16 illustrates an example container with each of its hatches opened simultaneously, according to an aspect of the present disclosure.

FIG. 16 illustrates an example container 1600 with each of its hatches 1610 opened simultaneously. Aspiration arms 1606A, 1606B, 1606A, 1606B are illustrated accessing module trays through the openings of the container 1600. For instance, the aspiration arms 1606A and 1606B may be first aspiration arms accessing mobile trays (e.g., upper trays) and the aspiration arms 1608A and 1608B may be second aspiration arms accessing fixed trays (e.g., lower trays). In this example, the hatches 1610 of the container 1600 may be opened and closed by a piston 1602 that pulls a cable 1604 that is joined with a lower edge of each hatch 1610. In other examples, the hatches 1610 may be opened and closed using other mechanisms that will be appreciated by one having skill in the art. In various instances, the container 1600 may also include end-of-travel sensors that sense when a hatch 1610 has been fully opened or fully closed. The container 1600 may also include sensors that detect when the aspiration arms 1606A, 1606B, 1606A, 1606B have been withdrawn from the container 1600 so that the hatches 1610 may be closed.

Figure 17:
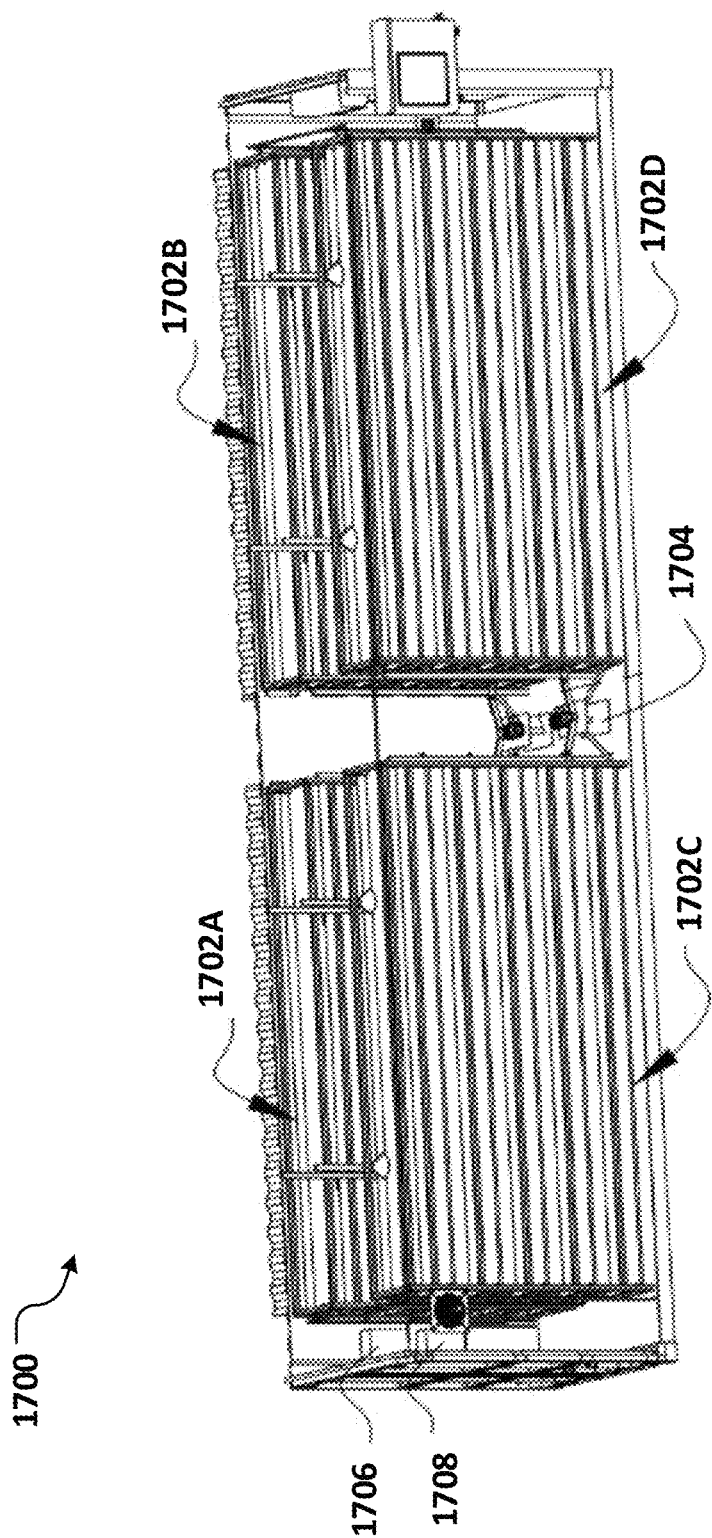
FIG. 17 illustrates an example container that includes four separate modules and an agitation unit, according to an aspect of the present disclosure.

FIG. 17 illustrates an example container 1700 that includes four separate modules 1702A, 1702B, 1702C, and 1702D. The example container 1700 also includes two agitation units 1704 (e.g., actuators), only one of which is shown in FIG. 17. Each agitation unit 1704 is configured to agitate or shake two modules, for instance, the modules on either side of the agitation unit 1704. In other examples, the container 1700 may include a single agitation unit or may include more than two. The agitation units 1704 of the container 1700 may be configured according to the description of the agitation unit 1206 above. The container 1700 may also include an electric supply panel 1706 and/or a pneumatic panel 1708 in communication with the agitation units 1704 as well as other components of the container 1700.

FIG. 18 illustrates a water distribution network of an example container 1800. The water distribution network includes the water distribution systems 1802A, 1802B, 1802C, 1802D of the respective modules in the container 1800. Each water distribution system 1802A, 1802B, 1802C, 1802D is constructed along the length of its respective module. A vertical tube extends each water distribution system a sufficient height to reach each of the rows of mobile trays. For example, the water distribution systems 1802C and 1802D include vertical tubes 1804A and 1804B, respectively. Multiple secondary tubes may extend from each vertical tube so that water is more directly introduced into each mobile tray. For example, the vertical tubes 1804A and 1804B include multiple secondary tubes 1806A and 1806B, respectively. The water supply takes place in the mobile trays over a hygroscopic material, not edible by either the larvae or by adult animals.

Figure 19:
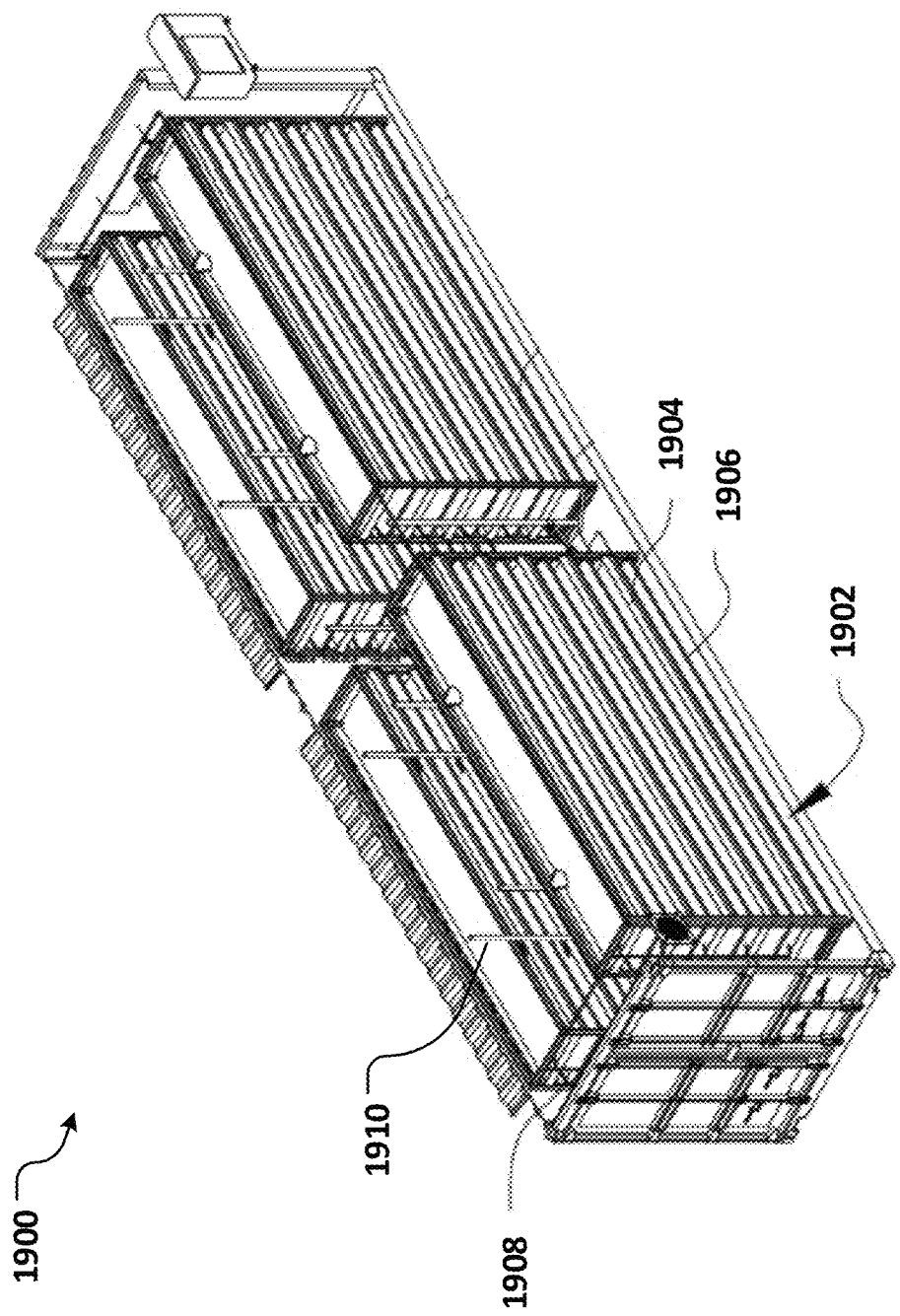
FIG. 19 illustrates an example container, according to an aspect of the present disclosure.

FIG. 19 illustrates an example container 1900 having multiple of the elements described herein. The container 1900 includes four modules 1902. Each of the modules 1902 includes multiple sets of a mobile tray 1902 and a fixed tray. The modules 1902 also each include a water distribution system 1908, which may be connected together to form a water distribution network. The container 1900 also includes two feed distribution columns 1910 for each module 1902. The feed distribution columns 1910 may be constructed according to the description of the feed distribution columns 10 above, but contained within the container 1900. In some instances, the container 1900 may include an aperture extending outside, which is configured to accept feed from a storage tank or other source. The aperture connects to the feed distribution columns 1910 using the feed distribution system described above.

In accordance with the preceding description, various example insect rearing operations are described below to illustrate the described components operating together. In one example, a moisture sensor positioned in mobile tray may communicate feedback to a control unit to indicate that a moisture level in the mobile tray is below a threshold. In response, the control unit causes water to be dispersed to the tray by activating a valve of the water distribution network. In some instances, the control unit may be programmed to disperse water to a tray immediately after, or soon after, feed is dispersed to the tray. In another example, feedback from one or more humidity sensors in the container indicate that a humidity level is below a threshold, which causes the control unit to cause water to be dispersed to one or more trays.

In various instances, the control unit may control humidity and/or temperature in conjunction with moisture levels. For example, the control unit may reduce an applied humidity by the container's air conditioning unit for a predetermined amount of time after water is dispersed to one or more trays. This may account for evaporation increasing a humidity level within the container. In another example, the control unit may increase a set temperature within the container, adjusting the air conditioning unit accordingly, after water is dispersed to one or more trays to account for the water temporarily lowering the ambient temperature in the one or more trays.

In some examples, the control unit may process data from sensors in multiple trays to provide control over insect rearing operations. For instance, while the water distribution network may be controlled to disperse water to a specific tray, every tray is exposed to changes in environment within the container (e.g., humidity and temperature). In some aspects, therefore, the control unit may be programmed to increase air flow in the container in response to large variations in temperature and/or humidity detected by one or more temperature and/or humidity sensors. In other aspects, such large variations in temperature and/or humidity may be detected by the control unit, which subsequently causes water dispersal from the water distribution network to specific trays that are detected as experiencing a greater effect from the large temperature and/or humidity variations. The localized water dispersal may help provide more consistency between the trays.

With respect to feed dispersal, the control unit may receive feedback from weight sensors positioned within or below the trays. The weight sensors detect a weight of the contents in a respective tray. When weight sensor feedback indicates a weight is below a threshold for a specific tray, the control unit may be programmed to cause feed to be dispersed to the specific tray from the feed distribution network by opening and closing valves as needed. If a hopper of a particular feed distribution column does not have sufficient feed, the control unit may cause feed to be distributed to the particular hopper. In various instances, the control unit is programmed to activate the agitation unit to agitate or shake the trays after feed is dispersed to a tray to evenly disperse the feed on the tray.

In another example, the control unit is programmed to determine when larvae should be harvested from particular trays in response to feedback from the weight sensors, motion sensors, and/or video cameras. The control unit may be programmed to make such a determination based on a weight meeting a threshold weight, or on a change in weight over time. For example, the control unit may receive data indicative that a tray contains 1 kg of insect, feed, and water at a first time. After 6 hours, the control unit receives data indicative that the weight is 0.8 kg. The loss of 20% mass within 6 hours may be indicative that the larvae are large enough for harvesting based on the quantity of food consumed during the time period. As such, the control may control the aspiration arms to collect the larvae and/or waste.

In other embodiments, the control unit detects larvae movement via a movement sensor or camera. Relatively large larvae may exhibit greater movement. After detecting such movement, the control unit may control the aspiration arms to collect the larvae and/or waste.

In various aspects, when the aspiration arms are needed, the control unit may be programmed to open a container's hatches (e.g., by activating a motor) to allow the aspiration arms to access the modules. The hatches may be opened individually, multiple at a time, or all at once. The control unit is programmed to then close the opened hatches after the aspiration arms have been removed. The container may include end-of-travel sensors to indicate, to the control unit, when the aspiration arms have been removed from the container to initiate closing the hatches.

In some examples, a portion of larvae may need to be collected for reproduction purposes. In such examples, the control unit may be programmed to cause the aspiration arms to collect larvae in a first container until a certain weight has been collected or until an aspiration arm has traveled a certain distance along a tray. After this threshold weight or distance has been reached, the control unit is programmed to cause the aspiration arms to collect the remaining larvae in a second container. This may include actuating valves for the piping 50, 51 for routing the larvae to the appropriate container in the reproduction area (e.g., via decanter 56, 60).

With respect to mobile trays in the reproduction area, in an example, such trays or their modules may include motion sensors. The motion sensors may detect movement of larvae after hatching from eggs. After a threshold amount of movement is detected, or an expected time period from first hatching has elapsed, the control unit may be programmed to control the aspiration arms to collect the larvae so they may be transferred to the container's growth area or to another container including growth modules. In another example, a weight sensor or a video sensor may be configured to detect the presence of eggs in a tray. After a threshold amount of eggs are detected, or an expected time period from first egg detection has elapsed, the control unit may be programmed to control the aspiration arms to collect the eggs.

In various instances, the control unit may generate an alert or alarm if feedback from one or more sensors exceeds a particular threshold.

While the above example insect rearing operations were described with respect to the presently disclosed container, it should be appreciated that similar operations may be performed in the presently disclosed insect rearing facility under the control of one or more control units. For instance, the one or more control units are programmed to control the various components in the reproduction area and growth area described in connection with FIGS. 3 and 4.

Feed Composition Embodiment

In some aspects of the present disclosure, a particular feed composition based on algae may be fed to the insects. For instance, the provided insect feed may be fed to *Tenebrio molitor* larvae. The particular feed composition may reduce the cost of food by incorporating marine algae and, as a side effect, the bioremediation for the degradation of the marine algae. Algae is subjected to the following treatment stages prior to its incorporation into the final feed. An inspection stage includes separating undesirable elements such as rock remains and plastic materials from the algae. A washing stage includes washing the algae with fresh water to eliminate any traces of sand, small crustaceans, and other unwanted elements, in addition to reducing the salinity. A drying stage includes drying the algae in the sun, which typically takes two to four days. The inventors have found that best results are achieved when the algae are placed in trays with forced air systems both above and below the algae, which improves drying times, and when the algae are kept away from plants and contact with animals or possible soil contamination. The algae is left to dry until moisture values in the range of 5 to 20% are obtained. A blending stage includes blending the dried algae by mixing and/or grinding.

The parameters of greatest interest to the dried algae's nutritional value are proteins, fats, carbohydrates, moisture, and ash. Table 1 below includes nutritional values of select compositions of dried algae.

TABLE 1

| Parameter | Value/100 g | | | | |
| --- | --- | --- | --- | --- | --- |
| | Genus Pyroia | Saccharina japonica | Undaria pinnatifida | Palmaria palmata | Units. |
| Energy value | 1485 | 745 | 698 | 937 | Kj |
| | 350 | 179 | 169 | 224 | Kcal |
| Fats | 0.1 | <0.5 | 2 | 0.5 | g |
| Saturated fats | 0.1 | 0.1 | 0.7 | 0.1 | g |
| Carbohydrates | 41 | 52 | 37 | 52 | g |
| Sugars | 6.2 | 0 | 0 | 0 | g |
| Proteins | 46.1 | 9.2 | 17 | 18 | g |
| Salt | 1.5 | 5.1 | 12.4 | 4.4 | g |
| Ashes | 5.1 | 24.5 | 31.5 | 16.2 | g |
| Moisture | 7.7 | 14.2 | 12.4 | 13.3 | g |

The presently disclosed feed composition includes composition ranges of Proteins 18-24%, Fats: 2-4%, Carbohydrates: 50-70%, Moisture: 5-20%, and Ashes: 1-8%. In various instances, the dried algae is mixed with one or more of the additives selected from the group consisting of wheat bran pellet, yeast extract, beetroot pulp, and alfalfa pellets. Additionally or alternatively, the feed composition may include one or more additives selected from the group consisting of Rapeseed and its flour, gluten pellets, beetroot pellets, rice husks, Golden DDG, dehydrated tomato, maize and its by-products, barley and its by-products, soy flour, and soy husk pellet. Table 2 below shows nutritional compositions of these additives.

TABLE 2

| Raw material | Protein | Fat | Moisture | Ashes | Carbohydrates | Sugars |
|---|---|---|---|---|---|---|
| Wheat bran pellet | 17.8 | 5.1 | 11.3 | 4.8 | 61 | 3.2 |
| Rapeseed flour | 41.2 | 1.9 | 9.8 | 3.2 | 43.9 | 7.1 |
| Gluten Pellet | 22.9 | 5.3 | 12.3 | 4.1 | 55.4 | 1.8 |
| Beetroot pellet | 28.8 | 1.6 | 7.2 | 5.3 | 57.1 | 6 |
| Beetroot pulp | 11 | 0.6 | 8.4 | 4.2 | 75.8 | 2.7 |
| Rice husks | 11.6 | 7.3 | 9.1 | 3.7 | 68.3 | 4.8 |
| Golden DDG | 33 | 9.5 | 10.4 | 4.4 | 42.7 | 5.2 |
| Dehydrated tomato | 5 | 14 | 35 | 6.2 | 39.8 | 13 |
| Maize | 7.3 | 3.3 | 13.6 | 1.1 | 74.7 | 1.7 |
| Barley | 11.3 | 1.7 | 11.1 | 2.2 | 73.7 | 1.6 |
| Soy Flour | 47 | 1.9 | 12 | 6.2 | 32.9 | 7 |
| Soy husk pellet | 11.8 | 2.5 | 11 | 4.7 | 70 | 1.5 |
| Rapeseed | 19 | 40.7 | 8.8 | 4 | 27.5 | 4 |
| Alfalfa pellets | 17.4 | 2.7 | 9.9 | 10.6 | 59.4 | 3.4 |
| Sunflower pellets | 5.7 | 3 | 8.6 | 3.3 | 79.4 | 0.7 |
| Yeast Extract | 45 | 6 | 5 | 6 | 38 | 0 |

The dried algae composes between 5% and 25% of the final feed composition. Example compositions of the provided feed composition are shown in Tables 3 to 5 below, and a control composition is shown in Table 6 below.

TABLE 3

Mix 1

| Raw material | Protein | Fat | Moisture | Ashes | Carbohydrates | Sugars | % Composition |
|---|---|---|---|---|---|---|---|
| Wheat bran pellet | 17.8 | 5.1 | 11.3 | 4.8 | 61 | 3.2 | 90% |
| Nori seaweed | 46.1 | 0.1 | 7.7 | 5.1 | 41 | 6.2 | 10% |
| Mixture | 20.63 | 4.6 | 10.94 | 4.83 | 59 | 3.5 | 100% |

TABLE 4

Mix 2

| Raw material | Protein | Fat | Moisture | Ashes | Carbohydrates | Sugars | % In the composition |
|---|---|---|---|---|---|---|---|
| Wheat bran pellet | 17.8 | 5.1 | 11.3 | 4.8 | 61 | 3.2 | 70% |
| *Palmaria palmata* (Dulse) | 18 | 0.5 | 13.3 | 26.2 | 52 | 0 | 20% |
| Yeast extract | 45 | 6 | 5 | 6 | 38 | 0 | 10% |
| Mixture | 20.56 | 4.27 | 11.07 | 9.2 | 56.9 | 2.24 | 100% |

TABLE 5

Mix 3

| Raw material | Protein | Fat | Moisture | Ashes | Carbohydrates | Sugars | % In the composition |
|---|---|---|---|---|---|---|---|
| Beetroot pulp | 11 | 0.6 | 8.4 | 4.2 | 75.8 | 2.7 | 50% |
| Alfalfa pellets | 17.4 | 2.7 | 9.9 | 10.6 | 59.4 | 3.4 | 30% |
| Nori seaweed | 46.1 | 0.1 | 7.7 | 5.1 | 41 | 6.2 | 20% |
| Mixture | 19.94 | 1.13 | 8.71 | 6.3 | 63.92 | 3.61 | 100% |

TABLE 6

Control

| Raw material | Protein | Fat | Moisture | Ashes | Carbohydrates | Sugars | % In the composition |
|---|---|---|---|---|---|---|---|
| Wheat bran pellet | 17.8 | 5.1 | 11.3 | 4.8 | 61 | 3.2 | 90% |
| Yeast extract | 45 | 6 | 5 | 6 | 38 | 0 | 10% |
| Mixture | 20.52 | 5.19 | 10.67 | 4.92 | 58.7 | 2.88 | 100% |

To demonstrate the effectiveness of the feeding and growth of the *Tenebrio molitor* larvae, different comparative studies have been carried out between the control composition shown in Table 6 and the example compositions shown in Tables 3 to 5. The results can be seen in Table 7 below.

TABLE 7

| | % of growth over initial weight | | | | |
|---|---|---|---|---|---|
| Days | 0 | 6 | 10 | 12 | 14 | 16 |
| Mix 1 | 0 | 11.9 | 22.6 | 37.4 | 46.4 | 48.6 |
| Mix 2 | 0 | 12.2 | 22.5 | 32.1 | 44.7 | 48.3 |
| Mix 3 | 0 | 10.7 | 17.6 | 27.2 | 38.0 | 44.2 |
| Control | 0 | 11.0 | 23.7 | 36.3 | 45.1 | 46.6 |

Figure 20:
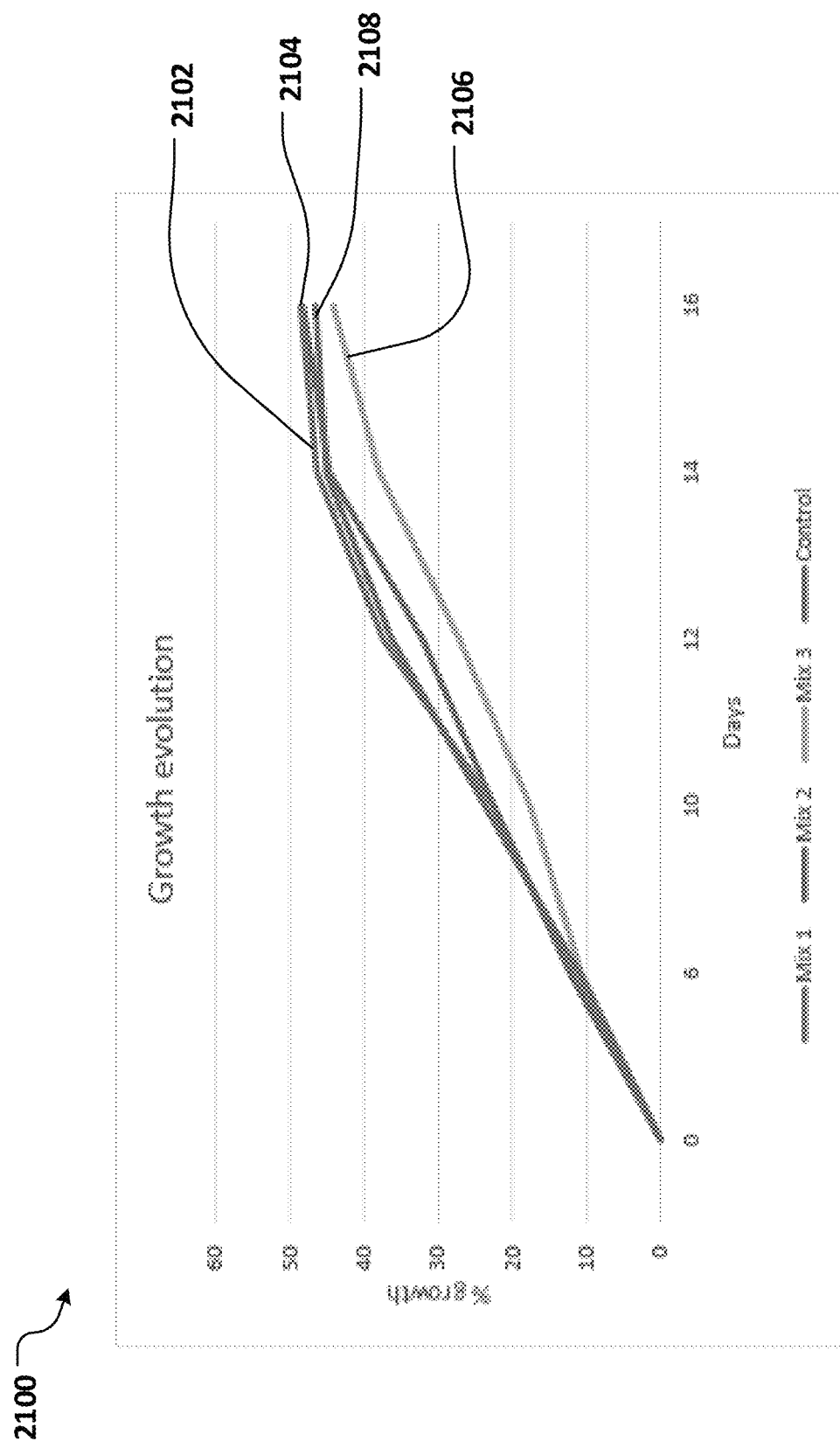
FIG. 20 illustrates a graph in which a growth evolution of *Tenebrio molitor* larvae is depicted with different example algae-based compositions, according to an aspect of the present disclosure.

FIG. 20 illustrates a graph 2100 in which the growth evolution of the *Tenebrio molitor* larvae is depicted with the different example algae-based compositions and the control composition. The Table 3 composition is the composition 2102. The Table 4 composition is the composition 2104. The Table 5 composition is the composition 2106. The control composition from Table 6 is the composition 2108. The graph illustrates that each of the compositions 2102, 2104, 2106, 2108 is substantially equivalent. Additionally, the example compositions 2102 and 2104 demonstrated a better growth percentage than the control composition 2108.

Additionally, the inventors have observed that the consumption of algae by the larvae contributes a specific coloring of the larvae that results from the ingestion of pigments such as chlorophyll (Chlorophyta), phycoerythrin, phycocyanin (Rhodophyta) and fucoxanthin (Phaeophyceae). This makes the product present different organoleptic characteristics due to the colouration presented by the larvae.

Accordingly, by feeding *Tenebrio molitor* larvae based on the provided feed composition that includes previously treated marine algae, raw material costs are reduced and ecological impacts invasive algae are reduced.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A system for automatically controlling insect rearing activities, the system comprising:
   a container including one or more modules configured with a plurality of trays, wherein the plurality of trays are partitioned into sets of trays having an upper tray with a sieved base and a lower tray to receive first objects that fall through the sieved base of the upper tray;
   a vacuum aspiration system including a vacuum and a plurality of sets of aspiration arms including a first aspiration arm and a second aspiration arm, the plurality of sets of aspiration arms configured to aspirate second objects through the first aspiration arm from the respective upper tray to a first collection tank and the first objects through the second aspiration arm from the respective lower tray to a second collection tank;
   a control unit programmed to control the plurality of sets of aspiration arms to collect the objects from the respective trays of the plurality of trays;
   one or more openings, wherein access to the one or more modules through the one or more openings is controlled by at least one retractable hatch;
   a light source configured to provide light to the interior of the container;
   at least one ventilation grille to allow air to enter the container;
   at least one air conditioning unit configured to maintain or adjust an internal humidity and internal temperature of the container;
   a light sensor configured to sense a lighting level in the container;
   a humidity sensor configured to sense the internal humidity of the container; and
   a temperature sensor configured to sense the internal temperature of the container.

2. The system of claim 1, wherein the control unit is programmed to at least one of:
   activate the at least one retractable hatch to open or close;
   adjust a lighting level output of the light source in response to feedback from the light sensor;
   adjust a humidity level output of the at least one air conditioning unit in response to feedback from the humidity sensor; or
   adjust a temperature level output of the at least one air conditioning unit in response to feedback from the temperature sensor.

3. The system of claim 2, wherein the control unit is programmed to adjust the temperature level output to a temperature between 25 and 30 degrees Celsius.

4. The system of claim 2, wherein the control unit is programmed to adjust the humidity level output to a humidity between 60% and 70%.

5. The system of claim 1, wherein the control unit is programmed to control the plurality of sets of aspiration arms to collect the objects from respective trays of the plurality of trays in response to at least one of a predetermined time elapsing or feedback from the plurality of weight sensors.

6. The container of claim 1, wherein the container is capable of being transported from a first location to a second location.

7. The system of claim 1, wherein the upper trays are connected to an actuator for shacking or agitating the upper trays, and
   wherein the control unit is programmed to cause the actuator to shake or agitate the upper trays.

8. The system of claim 1, wherein the one or more modules includes at least one reproduction module and at least one growth module, the reproduction module having upper trays with the sieved bases that include perforations with a first diameter, the growth module having upper trays with the sieved bases that include perforations with a second diameter, and wherein the first diameter is greater than the second diameter.

9. The system of claim 1, wherein the container further includes a video sensor configured to detect one or more of the first objects including insect eggs in the lower trays, wherein the control unit is programmed to control the plurality of sets of aspiration arms to collect the insect eggs from one or more respective lower trays of the plurality of trays in response to feedback from at least one of a plurality of weight sensors or the video sensor.

10. The system of claim 1, wherein the container further includes a plurality of motion sensors configured to detect movement, wherein the control unit is programmed to control the plurality of sets of aspiration arms to collect the second objects including insect larva from one or more respective upper trays of the plurality of trays in response to feedback from the plurality of motion sensors.

11. The system of claim 1, wherein the first objects aspirated through the respective second aspiration arms are at least one of insect eggs and waste, and the second objects aspirated through the respective first aspiration arms are at least one of insects and insect larva.

12. The system of claim 1, wherein the container further includes an air extractor configured to direct air within the container outside of the container.

13. A system for automatically controlling insect rearing activities, the system comprising:
    a container including one or more modules configured with a plurality of trays, wherein the plurality of trays are partitioned into sets of trays having an upper tray with a sieved base and a lower tray to receive first objects that fall through the sieved base of the upper tray;
    a vacuum aspiration system including a vacuum and a plurality of sets of aspiration arms including a first aspiration arm and a second aspiration arm, the plurality of sets of aspiration arms configured to aspirate second objects through the first aspiration arm from the respective upper tray to a first collection tank and the first objects through the second aspiration arm from the respective lower tray to a second collection tank;
    a control unit programmed to control the plurality of sets of aspiration arms to collect the objects from the respective trays of the plurality of trays;
    a feed distribution network configured to distribute feed from a feed source to the plurality of upper trays;
    a water distribution network configured to distribute water from a water source to the plurality of upper trays;
    a plurality of weight sensors configured to sense a respective weight of contents in a respective upper or lower tray of the plurality of trays; and
    a plurality of moisture sensors configured to sense a respective moisture level in a respective upper or lower tray of the plurality of trays.

14. The system of claim 13, wherein the control unit is programmed to at least one of:
    activate the feed distribution network to distribute feed to a respective upper tray of the plurality of trays in response to feedback from the plurality of weight sensors; or
    activate the water distribution network to distribute water to a respective upper tray of the plurality of trays in response to feedback from the plurality of moisture sensors.

15. The system of claim 13, wherein the feed distribution network is configured to simultaneously distribute feed to each of the respective upper trays of the plurality of trays.

16. The system of claim 13, wherein the water distribution network is configured to simultaneously distribute water to each of the respective upper trays of the plurality of trays.

17. The system of claim 13, wherein the control unit is programmed to activate the feed distribution network to distribute feed to a respective upper tray by opening a valve of the feed distribution network corresponding to the respective upper tray.

* * * * *